US008039238B2

(12) United States Patent
Saito et al.

(10) Patent No.: US 8,039,238 B2
(45) Date of Patent: Oct. 18, 2011

(54) METHOD OF CONTROLLING ETHANOL PRODUCTION AND MASS PRODUCTION OF LACTIC ACID AND TRANSFORMANT THEREFOR

(75) Inventors: Satoshi Saito, Toyota (JP); Osamu Saotome, Nissin (JP); Noriko Yasutani, Nagoya (JP); Yasuo Matsuo, Okazaki (JP); Nobuhiro Ishida, Aichi-ken (JP); Masana Hirai, Seto (JP); Takao Imaeda, Nisshin (JP); Chikara Miyazaki, Aichi-ken (JP); Kenro Tokuhiro, Aichi-ken (JP)

(73) Assignee: Toyota Jidosha Kabushiki Kaisha, Toyota-shi, Aichi-ken (JP)

( * ) Notice: Subject to any disclaimer, the term of this patent is extended or adjusted under 35 U.S.C. 154(b) by 470 days.

(21) Appl. No.: 10/507,129

(22) PCT Filed: Mar. 11, 2003

(86) PCT No.: PCT/JP03/02833
§ 371 (c)(1),
(2), (4) Date: Apr. 11, 2005

(87) PCT Pub. No.: WO03/076630
PCT Pub. Date: Sep. 18, 2003

(65) Prior Publication Data
US 2005/0214915 A1 Sep. 29, 2005

(30) Foreign Application Priority Data
Mar. 11, 2002 (JP) ................. 2002-065880

(51) Int. Cl.
C12P 7/40 (2006.01)
C12N 1/18 (2006.01)
C12N 15/74 (2006.01)
(52) U.S. Cl. ............... 435/136; 435/254.21; 435/483
(58) Field of Classification Search .............. None
See application file for complete search history.

(56) References Cited

U.S. PATENT DOCUMENTS

| 6,429,006 | B1 * | 8/2002 | Porro et al. | 435/254.2 |
| 2007/0105202 | A1 * | 5/2007 | Ishida et al. | 435/135 |
| 2009/0275095 | A1 * | 11/2009 | Ishida et al. | 435/139 |

FOREIGN PATENT DOCUMENTS

| JP | 2001-516584 | | 10/2001 |
| WO | WO99/14335 | * | 3/1999 |
| WO | WO 99/14335 | | 3/1999 |

OTHER PUBLICATIONS

Wolcott (Clinical Microbiology Reviews, Oct. 1992, p. 370-386).*
Gress et al. (Mammalian Genome 3: 609-619, 1992).*
Porro, Danilo, et al., "Replacement of a Metabolic Pathway for Large-Scale Production of Lactic Acid from Engineered Yeasts," *Applied Environ. Microbiol.*, vol. 65, No. 9 (Sep. 1999), pp. 4211-4215.
Bianchi, M. M., et al., "Efficient Homolactic Fermentation by *Kluyveromyces lactis* Strains Defective in Pyruvate Utilization and Transformed with the Heterologous LDH Gene," *Applied Environ. Microbiol.*, vol. 67, No. 12 (Dec. 2001) pp. 5621-5625.
"Development of Metabolically Engineered *Saccharomyces cerevisiae* Cells for the Production of Lactic Acid", Danilo Porro et al., Biotechnol. Prog., pp. 294-298, 1995.
"Analysis of the primary structure and promoter function of a pyruvate decarboxylase gene (PDCI) from *Saccharomyces cerevisiae*", Elkc Kellermann et al., Nucleic Acids Research, vol. 14, No. 22, 1986.
"Modification of Metabolic Pathways of *Saccharomyces cerevisiae* by the Expression of Lactate Dehydrogenase and Deletion of Pyruvate Decarboxylase Genes for the Lactic Acid Fermentation at Low pH Value", Eri Adachi et al., Journal of Fermentation and Bioengineering, vol. 86, No. 3, 284-289, 1998.
"Modification of Pig Heart Lactate Dehydrogenase with Methyl Methanethiosulphonate to Produce an Enzyme with Altered Catalytic Activity", D.P. Bloxham, Biochemical Journal, 161, 643-651, 1977.
"Primary Structure of Bovine Lactate Dehydrogenase-A Isozyme and its Synthesis in *Escherichia coli*", Naotaka Ishiguro, et al., Gene 91, pp. 281-285, 1990.
"Efficient Homolactic Fermentation by *Kluyveromyces lactis* Strains Defective in Pyruvate Utilization and Transformed with the Heterologous LDH Gene", Michele M. Bianchi et al., Applied and Environmental Microbiology, pp. 5621-5625, Dec. 2001.
"Replacement of a Metabolic Pathway for Large-Scale Production of Lactic Acid from Engineered Yeasts", Danilo Porro et al., Applied and Environmental Microbiology, vol. 65, No. 9, pp. 4211-4215, Sep. 1999.
Li, S. et al., "Molecular Features and Immunological Properties of Lactate Dehydrogenase $C_4$ Isozymes from Mouse and Rate Testes," J. Biol. Chem., 258(11):7017-28 (1983).
Kellerman E., et al., "Analysis of the Primary Structure and Promoter Function of a Pyruvate Decarboxylase Gene (*PDC1*) from *Saccharomyces cerevisiae*," Nucleic Acids Res., 14(22):8963-77 (1986).
Current Protocols in Molecular Biology (vol. 2 at pp. 1-4, Frederick M. Ausubel et al. eds., 1987-).
Molecular Cloning: A Laboratory Manual ($2^{nd}$ ed. at pp. xxxii-xxxiv, J. Sambrook et al. eds., 1989).
Porro et al., Biotechnol. Prog., 1995, vol. 11, pp. 294-298.
Adachi et al., Journal of Fermentation and Bioengineering, 1998, vol. 86, No. 3, pp. 284-289.

(Continued)

*Primary Examiner* — Scott Long
(74) *Attorney, Agent, or Firm* — Finnegan, Henderson, Farabow, Garrett & Dunner, LLP

(57) ABSTRACT

The present invention provides a transformant into which has been incorporated DNA for coding a foreign protein having lactate dehydrogenase activity and provided with pyruvic acid substrate affinity that equals or exceeds the pyruvic acid substrate affinity of the pyruvate decarboxylase inherent in the host organism. Said transformant can stably mass-produce lactic acid inside a host organism having the pyruvate decarboxylase gene.

4 Claims, 15 Drawing Sheets

OTHER PUBLICATIONS

Bianchi et al., Applied and Environmental Microbiology, 2001, vol. 67, No. 12, pp. 5621-5625.

Porro et al., Applied and Environmental Microbiology, 1999, vol. 65, No. 9, pp. 4211-4215.

Kellermann et al., Nucleic Acids Research, 1986, vol. 14, No. 22, pp. 8963-8977.

Japanese Office Action mailed Jan. 6, 2009.

Ishida et al., Appl. Environ. Microbiol. 2005, vol. 71, No. 4, pp. 1964-1970.

Current Protocols in Molecular Biology, Chapter 13, Unit 13.4 (John Wiley & Sons, Jan. 1993) (http://www.currentprotocols.com/protocol/mb1304 (online posting date: May 2001)).

* cited by examiner

| | | | | | | | |
|---|---|---|---|---|---|---|---|
| Phe | UUU | 26.0(146412) | Ser UCU | 23.6(132621) | Tyr UAU | 18.8(105557) | Cys UGU 8.0( 44797) |
| | UUC | 18.2(102353) | UCC | 14.2( 79920) | UAC | 14.7( 82477) | UGC 4.7( 26363) |
| Leu | UUA | 26.4(148212) | UCA | 18.8(105618) | UAA | 1.0(  5537) | UGA 0.6(  3456) |
| | UUG | 27.1(152577) | UCG | 8.6( 48192) | UAG | 0.5(  2629) | UGG 10.3( 58084) |
| | CUU | 12.2( 68500) | Pro CCU | 13.6( 76383) | His CAU | 13.7( 77276) | CGU 6.5( 36513) |
| | CUC | 5.4( 30213) | CCC | 6.8( 38245) | CAC | 7.8(438867) | CGC 2.6( 14559) |
| | CUA | 13.4( 75415) | CCA | 18.2(102307) | CAA | 27.5(154545) | CGA 3.0( 16965) |
| | CUG | 10.4( 58568) | CCG | 5.3( 29760) | Gln CAG | 12.2( 68453) | CGG 1.7(  9806) |
| Ile | AUU | 30.2(169875) | Thr ACU | 20.2(113664) | Asn AAU | 36.0(202449) | AGU 14.2( 79666) |
| | AUC | 17.1( 96127) | ACC | 12.6( 70760) | AAC | 24.9(140174) | AGC 9.7( 54339) |
| | AUA | 17.8(100079) | ACA | 17.7( 99786) | Lys AAA | 42.1(236838) | AGA 21.3(119693) |
| Met | AUG | 20.9(117420) | ACG | 8.0( 44816) | AAG | 30.8(173181) | Arg AGG 9.3( 52060) |
| Val | GUU | 22.0(123771) | Ala GCU | 21.1(118604) | Asp GAU | 37.8(212747) | Gly GGU 23.9(134536) |
| | GUC | 11.6( 65195) | GCC | 12.6( 70752) | GAC | 20.3(114444) | GGC 9.7( 54619) |
| | GUA | 11.8( 66110) | GCA | 16.2( 91026) | Glu GAA | 45.9(258028) | GGA 10.9( 61498) |
| | GUG | 10.7( 60001) | GCG | 6.1( 34530) | GAG | 19.1(107579) | GGG 6.0( 33624) |

FIG. 1

```
Bovine LDH        1 ATGGCAACTCTCAAGGATCAGCTGATTCAGAATCTTCTTAAGGAAGAACATGTCCCCCAG   60
modified LDH KCB  1 .....T...T.G..A.....AT........A...T.GT.G..A...........T..A..A   60
                    ***** *** * ** ***** ******** *** * * ** ************** ** **

Bovine LDH       61 AATAAGATTACAATTGTTGGGGTTGGTGCTGTTGGCATGGCCTGTGCCATCAGTATCTTA  120
modified LDH KCB 61 .....A....T........T..............T.....T........T..TTC...T..G  120
                    ***** ****** ************* ****** ***** ***** ****** ** *** **

Bovine LDH      121 ATGAAGGACTTGGCAGATGAAGTTGCTCTTGTTGATGTCATGGAAGATAAACTGAAGGGA  180
modified LDH KCB 121 .....A..T.....T........T.G........T.............T....A..T  180
                    ***** ** ***** ************** * ******** ************ **** **

Bovine LDH      181 GAGATGATGGATCTCCAACATGGCAGCCTTTTCCTTAGAACACCAAAAATTGTCTCTGGC  240
modified LDH KCB 181 ..A........T.G......TTCTT.G..TT.G.....T............T.....T  240
                    ** *********** * ***** * ** ** **** ************* *****

Bovine LDH      241 AAAGACTATAATGTGACAGCAAAACTCCAGGCTGGTTATTATCACAGCTGGGGCACGTCAG  300
modified LDH KCB 241 .....T........T..T..T..T..T..AT..........T..T.....T..TA.A..A  300
                    ***** ********** ** ** ** ** ** ***** *** ** ***** ** * **

Bovine LDH      301 CAAGAGGGAGAGAGCCGTCTGAATTTGGTCCAGCGTAACGTGAACATCTTTAAATTCATC  360
modified LDH KCB 301 .....A.T..ATCTA.AT..........T...AA.A..T..T..T..T........T..T  360
                    ***** ** ** * **** ** * ** ** ** ************ **

Bovine LDH      361 ATTCCTAATATTGTAAAATACAGCCCGAAATTGCAAGTTGCTTGTTGTTTCCAATCCAGTC  420
modified LDH KCB 361 .....A........T.....TTCT.........T..A...T.G........T.........T  420
                    ***** ******** ***** **** *** * ************ ***********

Bovine LDH      421 GATATTTTGACCTATGTGGCTTGGAAGATAAGTGGCTTTCCCAAAAACCGTGTTATTGGA  480
modified LDH KCB 421 ............T.....T........A..TTC...T.....A.....TA.A........T  480
                    ************ ** ****** ** **** ****** * **********

Bovine LDH      481 AGTGGTTGCAATCTGGATTCAGCTCGCTTCCGTTATCTCATGGGGGAGAGGCTGGGAGTT  540
modified LDH KCB 481 TC......T...T........T...A.A..TA.A...T.G.....T..A..AT....T...  540
                    ****** *** ********* **** * *** ** ** *** ** ** ***** ***

Bovine LDH      541 CACCCATTAAGCTGCCATGGGTGGATCCTTGGGGAGCATGGTGACTCTAGTGTGCCTGTA  600
modified LDH KCB 541 ..T.....GTCT..T.....T.....TT.G..T..A........T...TC...T..A..T  600
                    ** ****** ** ****** ***** * ** ** *********** **** **** ** **

Bovine LDH      601 TGGAGTGGAGTGAATGTTGCTGGTGTCTCCCTGAAGAATTTACACCCTGAATTAGGCACT  660
modified LDH KCB 601 ...TC...T..T..............T..TT....A.....G..T..A.....G..T...  660
                    *** **** ** ***************** ***** ** ** ** ** ***** ** ***

Bovine LDH      661 GATGCAGATAAGGAACAGTGGAAAGCGGTTCACAAACAAGTGGTTGACAGTGCTTATGAG  720
modified LDH KCB 661 .....T.....A.....A.....T.....T........T.........TTC.........A  720
                    ***** ***** ***** ***** ************** ************** *******

Bovine LDH      721 GTGATCAAACTGAAAGGCTACACATCCTGGGCCATTGGACTGTCAGTGGCCGATTTGGCA  780
modified LDH KCB 721 ..T..T...T........T..T..T..T.....T......TT.....T..T..T.........T  780
                    ** ** *** ******* ** ** ** ** ***** ****** ** ** ***********

Bovine LDH      781 GAAAGTATAATGAAGAATCTTAGGCGGGTGCATCCGATTTCCACCATGATTAAGGGTCTC  840
modified LDH KCB 781 ...TC...T.....A...T.G..AA.A..T.....A.....T..T........A...T.G  840
                    *** *** ***** *** * ** ***** ***** ** ***** ** ***********

Bovine LDH      841 TATGGAATAAAAGAGGATGTCTTCCTTAGTGTTCCTTGCATCTTGGGACAGAATGGAATC  900
modified LDH KCB 841 .....T..T.....A.....T..TT.GTC......A.T..T.....T..A.....T..T  900
                    ***** ** ****** ** * ********** ** ** ****** ** ****** **

Bovine LDH      901 TCAGACGTTGTGAAAGTGACTCTGACTCATGAAGAAGAGGCCTGTTTGAAGAAGAGTGCA  960
modified LDH KCB 901 ..T..T.....T.....T..T.............A.T.....A..ATC...T  960
                    ** ** ***** ***** * ************** ** ***** **

Bovine LDH      961 GATACACTTTGGGGGATCCAGAAAGAACTGCAGTTTTAA  999
modified LDH KCB 961 .....TT.G.....T..T..A......T....A......  999
                    ***** * ****** ** ** ****** **** *******
```

FIG. 2

Plasmid name: pBTrp-PDC1-LDHKCB
Plasmid size: 7.13 kb

BOVINE-MUSCLE-DERIVED
L-LACTATE DEHYDROGENASE (SIGMA) → Km=0.1mM y=3E-05x + 0.0003

YEAST-DERIVED PYRUVATE DECARBOXYLASE (SIGMA) → Km=0.346mM y=0.0006x + 0.0017

SEQUENCE LISTING

```
<160> NUMBER OF SEQ ID NOS: 39

<210> SEQ ID NO 1
<211> LENGTH: 332
<212> TYPE: PRT
<213> ORGANISM: Bovine

<400> SEQUENCE: 1

Met Ala Thr Leu Lys Asp Gln Leu Ile Gln Asn Leu Leu Lys Glu Glu
  1               5                  10                  15

His Val Pro Gln Asn Lys Ile Thr Ile Val Gly Val Gly Ala Val Gly
                 20                  25                  30

Met Ala Cys Ala Ile Ser Ile Leu Met Lys Asp Leu Ala Asp Glu Val
             35                  40                  45

Ala Leu Val Asp Val Met Glu Asp Lys Leu Lys Gly Glu Met Met Asp
         50                  55                  60
```

```
Leu Gln His Gly Ser Leu Phe Leu Arg Thr Pro Lys Ile Val Ser Gly
 65                  70                  75                  80

Lys Asp Tyr Asn Val Thr Ala Asn Ser Arg Leu Val Ile Ile Thr Ala
                 85                  90                  95

Gly Ala Arg Gln Gln Glu Gly Glu Ser Arg Leu Asn Leu Val Gln Arg
            100                 105                 110

Asn Val Asn Ile Phe Lys Phe Ile Ile Pro Asn Ile Val Lys Tyr Ser
        115                 120                 125

Pro Asn Cys Lys Leu Leu Val Val Ser Asn Pro Val Asp Ile Leu Thr
    130                 135                 140

Tyr Val Ala Trp Lys Ile Ser Gly Phe Pro Lys Asn Arg Val Ile Gly
145                 150                 155                 160

Ser Gly Cys Asn Leu Asp Ser Ala Arg Phe Arg Tyr Leu Met Gly Glu
                165                 170                 175

Arg Leu Gly Val His Pro Leu Ser Cys His Gly Trp Ile Leu Gly Glu
            180                 185                 190

His Gly Asp Ser Ser Val Pro Val Trp Ser Gly Val Asn Val Ala Gly
        195                 200                 205

Val Ser Leu Lys Asn Leu His Pro Glu Leu Gly Thr Asp Ala Asp Lys
    210                 215                 220

Glu Gln Trp Lys Ala Val His Lys Gln Val Val Asp Ser Ala Tyr Glu
225                 230                 235                 240

Val Ile Lys Leu Lys Gly Tyr Thr Ser Trp Ala Ile Gly Leu Ser Val
                245                 250                 255

Ala Asp Leu Ala Glu Ser Ile Met Lys Asn Leu Arg Arg Val His Pro
            260                 265                 270

Ile Ser Thr Met Ile Lys Gly Leu Tyr Gly Ile Lys Glu Asp Val Phe
        275                 280                 285

Leu Ser Val Pro Cys Ile Leu Gly Gln Asn Gly Ile Ser Asp Val Val
    290                 295                 300

Lys Val Thr Leu Thr His Glu Glu Ala Cys Leu Lys Lys Ser Ala
305                 310                 315                 320

Asp Thr Leu Trp Gly Ile Gln Lys Glu Leu Gln Phe
                325                 330
```

<210> SEQ ID NO 2
<211> LENGTH: 971
<212> TYPE: DNA
<213> ORGANISM: Saccharomyces cerevisiae

<400> SEQUENCE: 2

```
aagggtagcc tccccataac ataaactcaa taaaatatat agtcttcaac ttgaaaaagg    60
aacaagctca tgcaaagagg tggtacccgc acgccgaaat gcatgcaagt aacctattca   120
aagtaatatc tcatacatgt ttcatgaggg taacaacatg cgactgggtg agcatatgct   180
ccgctgatgt gatgtgcaag ataaacaagc aagacggaaa ctaacttctt cttcatgtaa   240
taaacacacc ccgcgtttat ttacctatct ttaaacttca acaccttata tcataactaa   300
tatttcttga gataagcaca ctgcacccat accttcctta aaagcgtagc ttccagtttt   360
tggtggttcc ggcttccttc ccgattccgc ccgctaaacg catattttg ttgcctggtg    420 gcatttgcaa aatgcataac ctatgcattt aaaagattat gtatgctctt ctgacttttc   480
gtgtgatgaa gctcgtggaa aaatgaata atttatgaat ttgagaacaa ttctgtgttg    540
ttacggtatt ttactatgga ataattaatc aattgaggat tttatgcaaa tatcgtttga   600
atatttttcc gaccctttga gtactttct tcataattgc ataatattgt ccgctgcccg     660
```

-continued

| | |
|---|---|
| tttttctgtt agacggtgtc ttgatctact tgctatcgtt caacaccacc ttatttctta | 720 |
| actattttt ttttagctca tttgaatcag cttatggtga tggcacattt ttgcataaac | 780 |
| ctagctgtcc tcgttgaaca taggaaaaaa aaatatatta acaaggctct ttcactctcc | 840 |
| ttgcaatcag atttgggttt gttccctttta ttttcatatt tcttgtcata ttcctttctc | 900 |
| aattattatt ttctactcat aaccacacgc aaaataacac agtcaaatca atcaaagatc | 960 |
| ccccaattct c | 971 |

<210> SEQ ID NO 3
<211> LENGTH: 999
<212> TYPE: DNA
<213> ORGANISM: Artificial Sequence
<220> FEATURE:
<223> OTHER INFORMATION: Description of Artificial Sequence:Modified DNA
      coding lactate dehydrogenase

<400> SEQUENCE: 3

| | |
|---|---|
| atggctactt tgaaagatca attgattcaa aatttgttga agaagaaca tgttccacaa | 60 |
| aataaaatta ctattgttgg tgttggtgct gttggtatgg cttgtgctat ttctattttg | 120 |
| atgaaagatt tggctgatga agttgctttg gttgatgtta tggaagataa attgaaaggt | 180 |
| gaaatgatgg atttgcaaca tggttctttg ttttgagaa ctccaaaaat tgtttctggt | 240 |
| aaagattata atgttactgc taattctaga ttggttatta ttactgctgg tgctagacaa | 300 |
| caagaaggtg aatctagatt gaatttggtt caaagaaatg ttaatatttt taaatttatt | 360 |
| attccaaata ttgttaaata ttctccaaat tgtaaattgt tggttgtttc taatccagtt | 420 |
| gatattttga cttatgttgc ttggaaaatt tctggttttc caaaaaatag agttattggt | 480 |
| tctggttgta atttggattc tgctagattt agatatttga tgggtgaaag attgggtgtt | 540 |
| catccattgt cttgtcatgg ttggattttg ggtgaacatg gtgattcttc tgttccagtt | 600 |
| tggtctggtg ttaatgttgc tggtgttcct ttgaaaaatt tgcatccaga attgggtact | 660 |
| gatgctgata agaacaatg gaaagctgtt cataaacaag ttgttgattc tgcttatgaa | 720 |
| gttattaaat tgaaaggtta tacttcttgg gctattggtt tgtctgttgc tgatttggct | 780 |
| gaatctatta tgaaaaattt gagaagagtt catccaattt ctactatgat taaaggtttg | 840 |
| tatggtatta agaagatgt ttttttgtct gttccatgta ttttgggtca aaatggtatt | 900 |
| tctgatgttg ttaaagttac tttgactcat gaagaagaag cttgtttgaa aaaatctgct | 960 |
| gatactttgt ggggtattca aaaagaattg caattttaa | 999 |

<210> SEQ ID NO 4
<211> LENGTH: 1052
<212> TYPE: DNA
<213> ORGANISM: Artificial Sequence
<220> FEATURE:
<223> OTHER INFORMATION: Description of Artificial Sequence:Modified DNA
      coding lactate dehydrogenase

<400> SEQUENCE: 4

| | |
|---|---|
| acagaattca caatggctac tttgaaagat caattgattc aaaatttgtt gaagaagaa | 60 |
| catgttccac aaaataaaat tactattgtt ggtgttggtg ctgttggtat ggcttgtgct | 120 |
| atttctattt tgatgaaaga tttggctgat gaagttgctt tggttgatgt tatggaagat | 180 |
| aaattgaaag gtgaaatgat ggatttgcaa catggttctt tgttttttgag aactccaaaa | 240 |
| attgtttctg gtaaagatta taatgttact gctaattcta gattggttat tattactgct | 300 |
| ggtgctagac aacaagaagg tgaatctaga ttgaatttgg ttcaaagaaa tgttaatatt | 360 |

-continued

```
tttaaattta ttattccaaa tattgttaaa tattctccaa attgtaaatt gttggttgtt      420
tctaatccag ttgatatttt gacttatgtt gcttggaaaa tttctggttt tccaaaaaat      480
agagttattg gttctggttg taatttggat tctgctagat ttagatattt gatgggtgaa      540
agattgggtg ttcatccatt gtcttgtcat ggttggattt tgggtgaaca tggtgattct      600
tctgttccag tttggtctgg tgttaatgtt gctggtgttt ctttgaaaaa tttgcatcca      660
gaattgggta ctgatgctga taaagaacaa tggaaagctg ttcataaaca agttgttgat      720
tctgcttatg aagttattaa attgaaaggt tatacttctt gggctattgg tttgtctgtt      780
gctgatttgg ctgaatctat tatgaaaaat ttgagaagag ttcatccaat ttctactatg      840
attaaaggtt tgtatggtat taagaagat gttttttttgt ctgttccatg tattttgggt      900
caaaatggta tttctgatgt tgttaaagtt actttgactc atgaagaaga agcttgtttg      960
aaaaaatctg ctgatacttt gtggggtatt caaaaagaat tgcaatttta ataactcgag      1020
cttggttgaa cacgttgcca aggcttaagt ga                                   1052
```

<210> SEQ ID NO 5
<211> LENGTH: 100
<212> TYPE: DNA
<213> ORGANISM: Artificial Sequence
<220> FEATURE:
<223> OTHER INFORMATION: Description of Artificial Sequence:primer

<400> SEQUENCE: 5

```
acagaattca caatggctac tttgaaagat caattgattc aaaatttgtt gaaagaagaa       60
catgttccac aaaataaaat tactattgtt ggtgttggtg                            100
```

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence:primer

<400> SEQUENCE: 6

```
acagaattca caatggctac                                                   20
```

<210> SEQ ID NO 7
<211> LENGTH: 100
<212> TYPE: DNA
<213> ORGANISM: Artificial Sequence
<220> FEATURE:
<223> OTHER INFORMATION: Description of Artificial Sequence:primer

<400> SEQUENCE: 7

```
atgataacaa ccacaaccac gacaaccata ccgaacacga taaagataaa actactttct       60
aaaccgacta cttcaacgaa accaactaca ataccttcta                            100
```

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence:primer

<400> SEQUENCE: 8

```
atgataacaa ccacaaccac                                                   20
```

<210> SEQ ID NO 9
<211> LENGTH: 100

```
<212> TYPE: DNA
<213> ORGANISM: Artificial Sequence
<220> FEATURE:
<223> OTHER INFORMATION: Description of Artificial Sequence:primer

<400> SEQUENCE: 9
tggttgatgt tatggaagat aaattgaaag gtgaaatgat ggatttgcaa catggttctt      60
tgtttttgag aactccaaaa attgtttctg gtaaagatta                           100

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence:primer

<400> SEQUENCE: 10
tggttgatgt tatggaagat                                                  20

<210> SEQ ID NO 11
<211> LENGTH: 100
<212> TYPE: DNA
<213> ORGANISM: Artificial Sequence
<220> FEATURE:
<223> OTHER INFORMATION: Description of Artificial Sequence:primer

<400> SEQUENCE: 11
taacaaagac catttctaat attacaatga cgattaagat ctaaccaata ataatgacga      60
ccacgatctg ttgttcttcc acttagatct aacttaaacc                           100

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence:primer

<400> SEQUENCE: 12
taacaaagac catttctaat a                                                21

<210> SEQ ID NO 13
<211> LENGTH: 100
<212> TYPE: DNA
<213> ORGANISM: Artificial Sequence
<220> FEATURE:
<223> OTHER INFORMATION: Description of Artificial Sequence:primer

<400> SEQUENCE: 13
tgaatctaga ttgaatttgg ttcaaagaaa tgttaatatt tttaaattta ttattccaaa      60
tattgttaaa tattctccaa attgtaaatt gttggttgtt                           100

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence:primer

<400> SEQUENCE: 14
tgaatctaga ttgaatttgg t                                                21

<210> SEQ ID NO 15
<211> LENGTH: 100
<212> TYPE: DNA
<213> ORGANISM: Artificial Sequence
```

```
<220> FEATURE:
<223> OTHER INFORMATION: Description of Artificial Sequence:primer

<400> SEQUENCE: 15
taacatttaa caaccaacaa agattaggtc aactataaaa ctgaatacaa cgaacctttt     60
aaagaccaaa aggtttttta tctcaataac caagaccaac                         100

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence:primer

<400> SEQUENCE: 16
taacatttaa caaccaacaa a                                              21

<210> SEQ ID NO 17
<211> LENGTH: 100
<212> TYPE: DNA
<213> ORGANISM: Artificial Sequence
<220> FEATURE:
<223> OTHER INFORMATION: Description of Artificial Sequence:primer

<400> SEQUENCE: 17
agagttattg gttctggttg taatttggat tctgctagat ttagatattt gatgggtgaa     60
agattgggtg ttcatccatt gtcttgtcat ggttggattt                         100

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence:primer

<400> SEQUENCE: 18
agagttattg gttctggttg t                                              21

<210> SEQ ID NO 19
<211> LENGTH: 100
<212> TYPE: DNA
<213> ORGANISM: Artificial Sequence
<220> FEATURE:
<223> OTHER INFORMATION: Description of Artificial Sequence:primer

<400> SEQUENCE: 19
cagaacagta ccaacctaaa acccacttgt accactaaga agacaaggtc aaaccagacc     60
acaattacaa cgaccacaaa gaaacttttt aaacgtaggt                         100

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence:primer

<400> SEQUENCE: 20
cagaacagta ccaacctaaa a                                              21

<210> SEQ ID NO 21
<211> LENGTH: 100
<212> TYPE: DNA
<213> ORGANISM: Artificial Sequence
<220> FEATURE:
<223> OTHER INFORMATION: Description of Artificial Sequence:primer
```

-continued

<400> SEQUENCE: 21
ctttgaaaaa tttgcatcca gaattgggta ctgatgctga taaagaacaa tggaaagctg    60
ttcataaaca agttgttgat tctgcttatg aagttattaa    100

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence:primer

<400> SEQUENCE: 22
ctttgaaaaa tttgcatcca g    21

<210> SEQ ID NO 23
<211> LENGTH: 100
<212> TYPE: DNA
<213> ORGANISM: Artificial Sequence
<220> FEATURE:
<223> OTHER INFORMATION: Description of Artificial Sequence:primer

<400> SEQUENCE: 23
agacgaatac ttcaataatt taactttcca atatgaagaa cccgataacc aaacagacaa    60
cgactaaacc gacttagata atacttttta aactcttctc    100

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence:primer

<400> SEQUENCE: 24
agacgaatac ttcaataatt t    21

<210> SEQ ID NO 25
<211> LENGTH: 100
<212> TYPE: DNA
<213> ORGANISM: Artificial Sequence
<220> FEATURE:
<223> OTHER INFORMATION: Description of Artificial Sequence:primer

<400> SEQUENCE: 25
tatgaaaaat tgagaagag ttcatccaat ttctactatg attaaaggtt tgtatggtat    60
taaagaagat gttttttgt ctgttccatg tattttgggt    100

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence:primer

<400> SEQUENCE: 26
atgaaaaatt tgagaagagt    20

<210> SEQ ID NO 27
<211> LENGTH: 100
<212> TYPE: DNA
<213> ORGANISM: Artificial Sequence
<220> FEATURE:
<223> OTHER INFORMATION: Description of Artificial Sequence:primer

<400> SEQUENCE: 27

```
gacaaggtac ataaaaccca gttttaccat aaagactaca acaatttcaa tgaaactgag      60
tacttcttct tcgaacaaac ttttttagac gactatgaaa                           100
```

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence:primer

<400> SEQUENCE: 28

```
gacaaggtac ataaaaccca g                                               21
```

<210> SEQ ID NO 29
<211> LENGTH: 60
<212> TYPE: DNA
<213> ORGANISM: Artificial Sequence
<220> FEATURE:
<223> OTHER INFORMATION: Description of Artificial Sequence:primer

<400> SEQUENCE: 29

```
aaaaaatctg ctgatacttt gtggggtatt caaaagaat tgcaatttta ataactcgag       60
```

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence:primer

<400> SEQUENCE: 30

```
aaaaaatctg ctgatacttt g                                               21
```

<210> SEQ ID NO 31
<211> LENGTH: 52
<212> TYPE: DNA
<213> ORGANISM: Artificial Sequence
<220> FEATURE:
<223> OTHER INFORMATION: Description of Artificial Sequence:primer

<400> SEQUENCE: 31

```
acgttaaaat tattgagctc gaaccaactt gtgcaacggt tccgaattca ct              52
```

<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence:primer

<400> SEQUENCE: 32

```
acgttaaaat tattgagctc g                                               21
```

<210> SEQ ID NO 33
<211> LENGTH: 31
<212> TYPE: DNA
<213> ORGANISM: Artificial Sequence
<220> FEATURE:
<223> OTHER INFORMATION: Description of Artificial Sequence:primer

<400> SEQUENCE: 33

```
atatatggat ccgcgtttat ttacctatct c                                    31
```

<210> SEQ ID NO 34
<211> LENGTH: 31

```
<212> TYPE: DNA
<213> ORGANISM: Artificial Sequence
<220> FEATURE:
<223> OTHER INFORMATION: Description of Artificial Sequence:primer

<400> SEQUENCE: 34
atatatgaat tctttgattg atttgactgt g                              31

<210> SEQ ID NO 35
<211> LENGTH: 34
<212> TYPE: DNA
<213> ORGANISM: Artificial Sequence
<220> FEATURE:
<223> OTHER INFORMATION: Description of Artificial Sequence:primer

<400> SEQUENCE: 35
atatatctcg aggccagcta acttcttggt cgac                           34

<210> SEQ ID NO 36
<211> LENGTH: 31
<212> TYPE: DNA
<213> ORGANISM: Artificial Sequence
<220> FEATURE:
<223> OTHER INFORMATION: Description of Artificial Sequence:primer

<400> SEQUENCE: 36
atatatgaat tctttgattg atttgactgt g                              31

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence:primer

<400> SEQUENCE: 37
tggttgatgt tatggaagat                                           20

<210> SEQ ID NO 38
<211> LENGTH: 21
<212> TYPE: DNA
<213> ORGANISM: Artificial Sequence
<220> FEATURE:
<223> OTHER INFORMATION: Description of Artificial Sequence:primer

<400> SEQUENCE: 38
gacaaggtac ataaaaccca g                                         21

<210> SEQ ID NO 39
<211> LENGTH: 19
<212> TYPE: DNA
<213> ORGANISM: Artificial Sequence
<220> FEATURE:
<223> OTHER INFORMATION: Description of Artificial Sequence:primer

<400> SEQUENCE: 39
gtaataaaca caccccgcg                                            19
```

METHOD OF CONTROLLING ETHANOL PRODUCTION AND MASS PRODUCTION OF LACTIC ACID AND TRANSFORMANT THEREFOR

TECHNICAL FIELD

The present invention relates to ethanol production control and a high-productivity technology for lactic acid, and more particularly to a high expression system suitable to lactic acid production using yeast.

BACKGROUND ART

Due to advances in recombinant DNA technology, technologies have been developed that obtain the target gene product by making a foreign gene express itself in a host such as a microbe, mold, animal, plant, or insect, and growing the gene's transformant. For example, by culturing yeast or the like, it is possible to produce a large volume of target gene product through fermentation production.

There have been several attempts to produce L-lactic acid using yeast. There have also been attempts to produce L-lactic acid by incorporating a bovine lactate dehydrogenase (LDH) gene into *Saccaromyces cerevisiae* (Eri Adhi et al., "Modification of metabolic pathway of *Saccaromyces cerevisiae* by the expression of lactate dehydrogenase and deletion of pyruvate genes for the lactic acid fermentation at low pH value," J. Ferment. Bioeng. Vol. 86, No. 3, 284-289, 1988; Danio Porro et al., "Development of metabolically engineered *Saccaromyces cerevisiae* cells for the production of lactic acid," Biotechnol. Prog. Vol. 11, 294-298, 1995, Kohyo (Japanese unexamined patent publication) No. 2001-516584). However, high-volume production of L-lactic acid was not observed in either of these reports.

It is known that the pyruvate decarboxylase in *Saccaromyces cerevisiae* has multiple isozymes. In ordinary yeast, pyruvate decarboxylase 1 is functioning. However, if this protein does not express itself due to the destruction of the main gene, etc., pyruvate decarboxylase 5 functions, thus maintaining ethanol production ("Autoregulation of yeast pyruvate decarboxylase gene expression requires the enzyme but not its catalytic activity," Ines Eberhardt, Hakan Cederberg, Haijuan Li, Stephen Koning, Frank Jordan and Stephen Hohmann, Eur. J. Biochem. Vol. 262, 191-201, 1999).

DISCLOSURE OF THE INVENTION

As explained above, a technology for producing L-lactic acid in high volume inside *Saccaromyces cerevisiae* has not previously been perfected.

One of the objectives of the present invention is to provide a technology to stably produce lactic acid in high volume by controlling the production of ethanol inside a host organism having a pyruvate decarboxylase gene, such as *Saccaromyces cerevisiae*.

The inventors of the present invention conducted research focusing on the lactate dehydrogenase (LDH) that is expressed during the production of lactic acid inside *Saccaromyces cerevisiae*, and discovered that a transformant, into which has been incorporated DNA for a foreign protein having lactate dehydrogenase activity and provided with pyruvic acid substrate affinity that equals or exceeds the pyruvic acid substrate affinity of the pyruvate decarboxylase inherent in the host organism, is effective for lactic acid production. Pyruvic acid is the common substrate for pyruvate decarboxylase, which leads to ethanol production; lactate dehydrogenase, which acts as a catalyst for lactic acid production; and the like. Now, in this transformant, lactate dehydrogenase has a higher level of substrate affinity to pyruvic acid than pyruvate decarboxylase; therefore, the ethanol production catalyzed by pyruvate decarboxylase is suppressed and the lactic acid production by the foreign lactate dehydrogenase is promoted. In this way, it is possible to increase lactic acid production by the transformant.

Based on the above findings, the following invention can be disclosed:

One aspect of the present invention is disclosed as a transformant, into which has been incorporated DNA for coding a foreign protein having lactate dehydrogenase activity and provided with pyruvic acid substrate affinity that equals or exceeds the pyruvic acid substrate affinity of the pyruvate decarboxylase inherent in the host organism. The present transformant also provides a transformant into which the aforementioned DNA for coding the foreign protein has been controllably incorporated by the promoter of the pyruvate decarboxylase gene on the host chromosome or by a homologue of said promoter that replaces said promoter.

The aforementioned foreign protein in the transformant according to the present invention should preferably be a bovine lactate dehydrogenase or its homologue. This protein would be especially effective if it were a protein consisting of the amino acid sequence shown in SEQ ID NO:1, or its homologue. Furthermore, said protein should preferably be coded by the DNA sequence shown in SEQ ID NO:3. This DNA sequence should preferably be held by the transformant as the DNA sequence shown in SEQ ID NO:4.

The aforementioned promoter on the host chromosome should preferably be a pyruvate decarboxylase 1 gene promoter. Furthermore, this promoter should preferably use the DNA sequence shown in SEQ ID NO:2 or its homologue.

In the present transformant, the aforementioned host organism should preferably be from the *Saccaromyces* family and more preferably be *Saccaromyces cerevisiae*.

Another aspect of the present invention is disclosed as a lactic acid manufacturing method provided with a process for culturing the present transformant and a process for separating lactic acid from the cultured product obtained in the aforementioned process. This method can stably and efficiently manufacture lactic acid.

BRIEF EXPLANATION OF DRAWINGS

FIG. 1

FIG. 1 is a diagram illustrating the Codon Usage method used for *Saccaromyces cerevisiae* and its usage frequency.

FIG. 2

FIG. 2 is a diagram illustrating the homologue analysis results of the base sequence in a bovine-derived LDH and the base sequence in a modified LDH. The top row indicates the base sequence in the bovine-derived LDH while the bottom row indicates the modified base sequence, in which the bases that are different from the base sequence in the bovine-derived LDH are indicated by symbols (A, T, C or G).

FIG. 3 is a diagram illustrating the primer structure for synthesizing a long-chain DNA by means of PCR used in Embodiment 1 and the synthesis steps (Steps 1 through 4).

FIG. 4 is a diagram illustrating the plasmid map of the constructed vector pBTrp-PDC1-LDHKCB.

FIG. 5 is a diagram illustrating a part of the process of constructing the vector shown in FIG. 5.

FIG. 6 is a diagram illustrating another part of the pBTrp-PDC1-LDH construction process.

FIG. 7 is a diagram illustrating another part of the pBTrp-PDC1-LDH construction process.

FIG. 8 is a diagram illustrating another part of the process (the last step) of constructing the vector shown in FIG. 5.

FIG. 9 is a diagram illustrating a structural change in the target site of the chromosome DNA in the transformant obtained in one embodiment.

FIG. 10 is a diagram illustrating the volume percentages of lactic acid and the ethanol produced in one embodiment.

FIG. 11 is a diagram illustrating the trends in the volume percentages of lactic acid and ethanol produced in one embodiment.

FIG. 12 is a diagram illustrating the pyruvic acid saturation curve of the bovine L-lactate dehydrogenase.

FIG. 13 is a diagram illustrating the Lineweaver-Burk plot of the bovine L-lactate dehydrogenase.

FIG. 14 is a diagram illustrating a part of the process for constructing a vector (pBTrp-PDC1P-LDH; 7.11 kb) having a DNA segment for coding the L-lactate dehydrogenase derived from the lactic bacterium *Bifidobacterium longum*.

FIG. 15 is a diagram illustrating another part of the process for constructing a vector (pBTrp-PDC1P-LDH; 7.11 kb) having a DNA segment for coding the L-lactate dehydrogenase derived from the lactic bacterium *Bifidobacterium longum*; this diagram illustrates a latter stage of the process shown in FIG. 14.

FIG. 16 is a diagram illustrating the pyruvic acid saturation curve of a pyruvate decarboxylase derived from yeast.

FIG. 17 is a diagram illustrating the Lineweaver-Burk plot of a pyruvate decarboxylase derived from yeast.

PREFERRED EMBODIMENTS OF THE INVENTION

Figure 3:
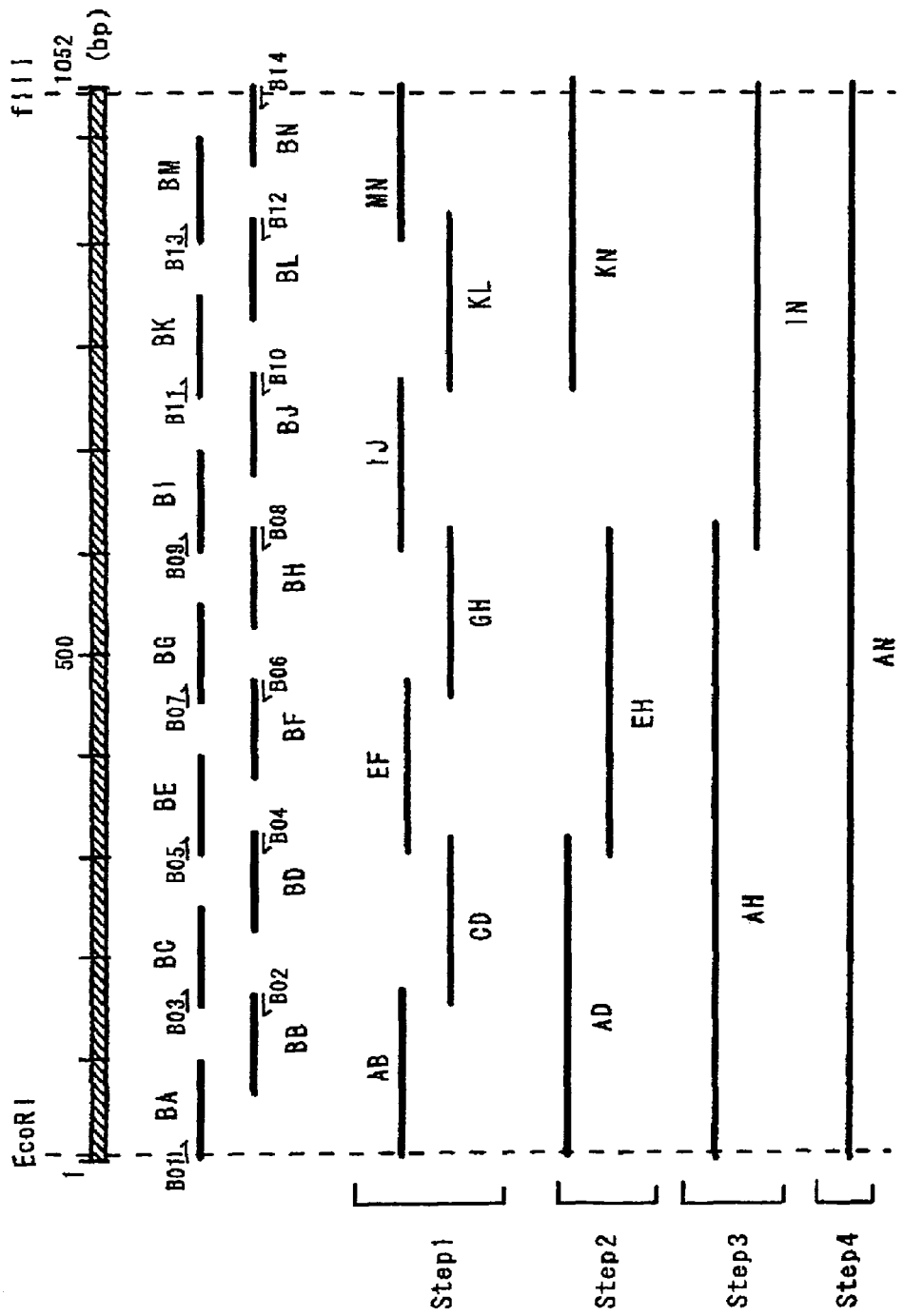
FIG. 3

Embodiments of the present invention are explained in detail below.
(Transformant)

The foreign protein that is expressed in the transformant has lactate dehydrogenase (LDH) activity, and, the transformant has pyruvic acid substrate affinity that equals or exceeds the pyruvic acid substrate affinity of this enzyme in its relationship with the pyruvate decarboxylase inherent in the host organism that is to be transformed.

The foreign protein that is expressed in the transformant has lactate dehydrogenase (LDH) activity, and in its relationship with the pyruvate decarboxylase inherent in the host organism that is to be transformed, has pyruvic acid substrate affinity that equals or exceeds the pyruvic acid substrate affinity of this enzyme.

Here, LDH is known as an enzyme that acts as a medium for a reaction that produces lactic acid from pyruvic acid in the glycolytic system of an organism such as yeast. Here, lactic acid includes L(+)-lactic acid and D(−)-lactic acid, but would preferably be L(+)-lactic acid. L(+)-lactic is produced by L(+)-LDH and D(−)-lactic acid is produced by D(−)-LDH.

LDH can be used as the foreign protein in the present invention. Various types of homologues exist depending on the type of organism, or even inside [single] organisms. In the present invention, the protein having LDH activity includes natural LDH as well as LDH that is artificially synthesized through chemical synthesis or genetic engineering.

The LDH should preferably be derived from a eucaryotic microbe such as yeast; and more preferably from a higher eucaryote, such as a plant, animal, or insect; and even more preferably from even higher eucaryotes, including mammals such as bovines. Bovine-derived LDH is the most preferable. An example of a bovine-derived LDH is the protein consisting of the amino acid sequence shown in SEQ ID NO:1.

Bovine-derived LDH that is derived from a muscle, a heart, or the like, is available and can be used. For the enzyme number, EC 1.1.1.27 can be used.

Furthermore, the foreign protein in the present invention includes homologues of these types of LDH. LDH homologues include proteins which has LDH activity, with one or several amino acids in an amino acid sequence of a naturally derived LDH replaced, void, inserted, and/or added; and proteins which also has LDH activity that are at least 70%, and more preferably at least 80%, homologous in their amino acid sequence to a naturally derived LDH.

Note that the number of variations within the amino acid sequence is not limited as long as the original protein function can be maintained, but should preferably be within 70% of the total number of amino acids, more preferably within 30%, and most preferably within 20%.

For example, a desirable homologue would be a protein with one or several amino acids in the amino acid sequence shown in SEQ ID NO:1 replaced, void, inserted, and/or added, and which has LDH activity; or a protein that is at least 70%, and more preferably at least 80%, homologous in its amino acid sequence to the amino acid sequence shown in SEQ ID NO:1, and which also has LDH activity.

Note that the homology in the sequence can be determined using a homology search tool such as one available from BLAST (http://blast.genome.ad.jp/), or FASTA (http://fast-a.genome.ad.jp/SIT/FASTA.html), etc.

Modification of amino acid sequence can be achieved by incorporating a variation that could be a replacement, void, an insertion, and/or an addition as needed into the amino acid sequence that is to be modified, using a site-specific dislocation incorporation method (Current Protocols I Molecular Biology edit. Ausubel et al., (1987) Publish. John Wily & Sons Selection 8.1-8.5), etc. Such a modification is not limited to artificial incorporation or synthesis of a variation, and includes those generated by artificial variation processes as well as those generated by amino acid variations in the natural world.

The foreign protein used in the present invention should preferably have high substrate affinity to pyruvic acid. Here, substrate affinity means the Km value in the Michaelis-Menten equation as shown in Formula (1).

Mathematical Expression 1

$$V_0 = k_2 E_0 [S]/([S]+Km) \qquad (1)$$

Note that $V_0$ is the steady-state initial speed, [S] is the substrate concentration, [ES] is the concentration of a compound consisting of the enzyme and the substrate, $E_0$ is the total concentration of the enzyme, $k_2$ is a speed constant for ES→E+S.

The Michaelis-Menten formula is based on the relationship among the substrate S, the enzyme E, the substrate-enzyme compound ES, and the product P, expressed by Formula (2) below. $k_1$ is the equilibrium constant when the product P and the enzyme E are generated from the compound ES, and $k_{-1}$ is the equilibrium constant when the compound ES is dissociated into the enzyme E and the substrate S.

Mathematical expression 2

$$E + S \underset{k_{-1}}{\overset{k_1}{\rightleftharpoons}} ES \overset{k_2}{\rightarrow} E + P \qquad (2)$$

Here, Km can be defined from the constants using Formula (3) below.
Mathematical Expression 3

$V_0 = k_2[ES]$ $k_1[E][S] = (k_2 + k_{-1})[ES]$ $$\frac{[E][S]}{[ES]} = \frac{k_2 + k_{-1}}{k_1} \qquad (3)$$
$$= K_m$$

Furthermore, as indicated by Formula (4), Km can be replaced with various concentrations.
Mathematical Expression 4

$Km = (E_0 - [ES])[S]/[ES]$ \qquad (4)

Substrate affinity can be determined by determining the relationship between the substrate concentration [S] and the initial speed $V_0$ under a constant enzyme concentration, using a graph that shows the substrate concentration on the horizontal axis and the initial speed on the vertical axis, for example. Substrate affinity can also be determined from a Lineweaver-Burk plot.

The pyruvic acid substrate affinity of the foreign protein in the present invention, in its relationship with the pyruvate decarboxylase inherent in the host organism, should preferably equal or exceed the pyruvic acid substrate affinity of this enzyme. Substrate affinity should preferably be compared under the same temperature and pH conditions, etc. The temperature and pH conditions can be determined by taking into consideration the environment in which these enzymes catalyze in the host organism. For example, the substrate affinity of these enzymes should preferably be measured under a temperature of between 30 and 37° C. and a pH of between 6.0 and 7.5.

The pyruvic acid substrate affinity of the foreign protein should preferably be approximately 1.5 mM or less. Because, if the pyruvic acid substrate affinity exceeds 1.5mM, the pyruvate decarboxylase of the host organism tends to react with pyruvic acid. More preferably, the value should be 1 mM or less. Even more preferably, the value should be 0.5 mM or less, and most preferably should be 0.1 mM or less.

Furthermore, the pyruvic acid substrate affinity of the foreign protein should preferably equal or exceed the pyruvic acid substrate affinity of the pyruvate decarboxylase of the host organism. If the pyruvic acid substrate affinity of the foreign is lower than the pyruvic acid substrate affinity of the pyruvate decarboxylase of the host organism, the pyruvate decarboxylase of the host organism tends to react with pyruvic acid. In this Specification, equal substrate affinities means that the corresponding substrate affinities, i.e., the Km values, are equal; a higher substrate affinity means that one substrate affinity (Km value) is lower than the other corresponding Km value.

A DNA for coding such a foreign protein has been incorporated into the present transformant. There is no restriction on the source of this DNA, which can be a cDNA, genome DNA, synthetic DNA, or the like.

Furthermore, this DNA may possess a naturally derived base sequence for coding LDH, or may be a DNA in which part or the whole of such a base sequence is modified and which codes a protein possessing LDH activity. It may also be a DNA possessing a naturally derived base sequence that codes or synthesizes an LDH homologue.

The DNA used in the present invention may possess a base sequence that uses the Codon Usage method, which is often used for the host organism to be transformed. For example, the present DNA may possess a base sequence that has been genetically coded using the Codon Usage method in the Saccaromyces family, especially Saccaromyces cerevisiae.

Note that a DNA can be chemically synthesized, or can be synthesized, using the method developed by Fujimoto et al. (Hideya Fujimoto, Synthetic Gene Creation Method, Plant Cell Engineering Series 7, Plant PCR Experiment Protocol, 1997, Shujunsha Co., Ltd., p 95-100), which is a known method for synthesizing long-chain DNA.
(DNA Structure)

By incorporating the DNA for coding the amino acid sequence of the foreign protein into the host organism and letting the protein coded by this DNA express itself, it is possible to produce lactic acid in the host cells.

For transformation, a DNA structure is used that can express a DNA segment comprised of the present DNA inside the host cells. The form of the DNA structure for transformation is not limited in any way, and plasmid (DNA), bacteriopharge (DNA), retrotranspozon (DNA), or an artificial chromosome (YAC, PAC, BAC, MAC, etc.) can be selected and adopted according to the incorporation mode (inside or outside the gene) for the foreign gene or the type of host cell. Furthermore, there is no structural restriction, such as linear or circular. Therefore, the DNA structure can be provided with the configuration segment of any of these vectors other than that of the present DNA itself. The preferred procaryotic cell vectors, eucaryotic cell vectors, animal cell vectors, and plant cell vectors are well known in the field Note that the plasmid DNA can, for example, be a YCp-type escherichia-yeast shuttle vector, such as pRS413, pRS415, pRS416, YCp50, pAUR112, or pAUR123; a YEp-type Escherichia-yeast shuttle vector, such as pYES32 or YEp13; a YIp-type escherichia-yeast shuttle vector, such as pRS403, pRS404, pRS405, pRS406, pAUR101, or pAUR135; a plasmid derived from escherichia (a ColE-type plasmid, such as pBR322, pBR325, pUC18, pUC19, pUC119, pTV118N, pTV119N, pBluescript, pHSG298, pHSG396, or pTrc99A; a p1A-type plasmid, such as pACYC177 or pACYC184; a pSC101-type plasmid, such as pMW118, pMW119, pMW218, pMW219; or the like); or a plasmid derived from Bacillus subtilis (PUB110, pTP5, etc.). The pharge DNA can be a λ pharge (Charon4A, Charon21A, EMBL3, EMBL4, λgt100, gt11, or zap), φX174, M13mp18, or M13mp19, for example. The retrotranspozon can be a Ty factor, for example. YAC can be pYACC2, for example.

The present DNA structure is produced by severing a fragment containing, for example, the present DNA, using an appropriate limiting enzyme, and inserting the fragment into the limiting enzyme site or multi-cloning site of the vector DNA being used.

The first form of the present DNA structure is provided with a promoter segment that links a DNA segment comprised of the present DNA, so that said DNA segment can express itself. In other words, the present DNA segment is controllably linked by the promoter to the downstream side of the promoter.

It is preferable to use yeast to express the present DNA product, i.e., a protein having LDH activity; and therefore, the use of a promoter that expresses itself inside yeast is preferable. For such a promoter, it is preferable to use a pyruvate decarboxylase gene promoter, gal1 promoter, gal10 promoter, heat shock protein promoter, MF.alpha.1 promoter, PH05 promoter, PGK promoter, GAP promoter, ADH promoter, or AOX1 promoter, for example. In particular, a pyruvate decarboxylase 1 gene promoter derived from the *Saccharomyces* family is preferable, and the use of the pyruvate decarboxylase 1 gene promoter derived from *Saccharomyces cerevisiae* is more preferable. This is because these promoters are expressed at high degrees in the ethanol fermentation route of the *Saccharomyces* family (*cerevisiae*). Note that said promoter sequence can be isolated using the PCR breeding method, which uses the genome DNA of the pyruvate decarboxylase 1 gene of a yeast in the *Saccharomyces* family as the mold. The base sequence of said promoter derived from *Saccharomyces cerevisiae* is shown in SEQ ID NO:2. For the promoter segment in the present DNA structure, it is possible to use a DNA comprised of the base sequence described in SEQ ID NO:2, as well as a DNA that is comprised of this base sequence with one or several bases void, replaced, or added, and which has promoter activity; or a DNA that is hybridized with a DNA formulated from some or all of the sequences in the base sequence shown in SEQ ID NO:2 or its complementary strand under stringent conditions and which has promoter activity (in other words, the homologue of said promoter).

The second or another form of the present DNA is provided with the present DNA as well as a DNA segment for homologously recombining the host chromosomes. The DNA segment for homologous recombination is a DNA sequence that is homologous to the DNA sequence in the vicinity of the target site in the host chromosome into which the DNA is to be incorporated. At least one, preferably two, DNA segments for homologous recombination should be provided. For example, two DNA segments for homologous recombination should preferably have DNA sequences homologous to the DNA on the upstream and downstream sides of the target site on the chromosome, and the present DNA should preferably be linked between these DNA segments.

When incorporating the present DNA into the host chromosome by means of homologous recombination, it is possible to incorporate the present DNA in a state that is controllable by a promoter on the host chromosome. In this case, by incorporating the present DNA, it is possible to simultaneously destroy the endogenous gene that should have been controlled by said promoter and to allow the present DNA, which is foreign, to express itself instead of the endogenous gene. This process is especially useful when said promoter is a highly expressive promoter in the host cell.

To create such an expression system on the host chromosome, it is preferable to target a high-expression gene in the host chromosome and to incorporate the present DNA into the downstream side of the promoter that controls this gene, so that the present DNA is controlled by the promoter. If an ethanol-fermenting microbe, such as yeast, is used as the host, it is possible to target a pyruvate decarboxylase gene (particularly, the pyruvate decarboxylase 1 gene) and incorporate a DNA for coding an LDH-active protein under the control of an endogenous pyruvate decarboxylase gene promoter. In this case, it is possible to make the DNA segment for homologous recombination homologous to the sequence in the structural gene region of the LDH of the pyruvate decarboxylase 1 gene or its vicinity (including the sequence near the start codon, the sequence on the upstream region of the start codon, and the sequence inside the structural gene). Preferably, an enzyme in the *Saccharomyces* family (especially *cerevisiae*) should be used as the host and a DNA structure that targets the pyruvate decarboxylase 1 gene in this host should be used. With such a DNA structure, the destruction of the pyruvate decarboxylase 1 gene and replacement of this structural gene with LDH can be achieved using only a single vector. Because the pyruvate decarboxylase 1 gene is an enzyme that mediates the irreversible reaction from pyruvic acid to acetoaldehyde, the destruction of its gene can be expected to suppress the production of ethanol via acetoaldehyde, and at the same time promote the production of lactic acid by LDH, which uses pyruvic acid as the substrate.

Even the first DNA structure can be made into a DNA structure for homologous recombination by providing it with a DNA segment for homologous recombination with the host chromosome. In the first DNA structure, the promoter segment inside the DNA structure can also be used as the DNA segment for homologous recombination. For example, for the host *Saccharomyces cerevisiae*, a DNA structure that has the promoter in the *Saccharomyces cerevisiae* host chromosome, e.g., the pyruvate decarboxylase 1 gene promoter as a promoter segment comprises a targeting vector that has said gene 1 as the target site. In this case, the first DNA structure should preferably be provided with a sequence homologous to the structural gene region of the pyruvate decarboxylase 1 gene.

Note that it is possible to link to the DNA structure, a terminator, and as needed, a cis-element such as an enhancer, a splicing signal, a polyA additional signal, a selective marker, or a ribosome bond sequence (SD sequence). There are no special restrictions on the selective marker, and various types of known marker genes can be used, such as drug-resistant genes or auxotrophic genes. For example, the dihydrofolate reductase gene, ampicilin-resistant gene, neomycin-resistant gene, or the like can be used.

(Transformation by DNA Structure)

Once a DNA structure has been built, it can be incorporated into an appropriate host cell by means of an appropriate method, such as the transformation method, the transfection method, the bonding method, protoplast fusion, the electropolation method, the lipofection method, the lithium acetate method, the particle gun method, the calcium phosphate precipitation method, the agrobacterium method, the PEG method, or the direct microinjection method. After the incorporation of the DNA structure, the recipient cell is cultured in a selective media.

For the host cell, it is possible to use a bacterium such as *Escherichia coli* or *Bacillus subtilis;* a yeast such as *Saccharomyces cerevisiae, Saccharomyces pombe,* or *Pichia pastoris;* an insect cell such as sf9 or sf21; an animal cell such as a COS cell or a Chinese hamster ovarian cell (CHO cell); or a plant cell from sweet potato, tobacco, or the like. The host cell should preferably be a microbe, such as yeast, that causes alcoholic fermentation, or an acid-resistant microbe, examples of which include yeasts represented by the *Saccaromyces* family, such as *Saccaromyces cerevisiae*. Specific examples include the *Saccaromyces cerevisiae* IF02260 strain and YPH strain.

In the transformant created by the DNA structure, the structural components of the DNA structure are present on the chromosomes or extrachromosomal elements (including artificial chromosomes). If the DNA structure is maintained outside the chromosome or is incorporated into the chromosome based on random integration, other types of yeast that use pyruvic acid, which is the substrate for LDH, as the substrate, e.g., the pyruvate decarboxylase gene (the pyruvate decarboxylase 1 gene in the case of yeasts belonging to the Saccaromyces family), should preferably be knocked out by the targeting vector.

When the DNA structure that is described above and that can achieve homologous recombination is incorporated, a DNA segment, which is the present DNA controllably linked by the desired promoter on the host chromosome, is present on the downstream side of said promoter or a homologue of said promoter that replaces said promoter. In the transformant of a yeast in the Saccaromyces family, it is preferable to provide the present DNA on the downstream side of the pyruvate decarboxylase 1 gene promoter on the host chromosome or a homologue of said promoter that replaces said promoter, so that the present DNA can be controlled by said promoter.

Furthermore, a selective marker gene and part of the destroyed structural gene (at the site corresponding to the homologous sequence on the DNA structure) are normally present on the downstream side of the present DNA in a homologous recombinant.

Whether or not the present DNA has been incorporated under the desired promoter can be checked using the PCR method or the Southern hybridization method. For example, it is possible to check this by formulating DNA from the transformant, performing PCR with an incorporation site-specific primer, and detecting the expected band from the PCR product in electrophoresis. Alternatively, it is also possible to perform PCR with a primer that has been marked with a fluorescent dye, etc. These methods are known to those skilled in the art.

(Manufacturing of Lactic Acid)

Culturing the transformant obtained by incorporating the DNA structure produces lactic acid, which is an expression product of the foreign gene, in the cultured product. Lactic acid can then be obtained by separating it from the cultured product. In the present invention, "cultured product" includes the culture supernatant, as well as the cultured cell or microbe, and the crushed form of the cell or microbe.

For culturing the transformant according to the present invention, the culturing conditions can be selected according to the type of transformant. These culturing conditions are known to those skilled in the art.

For the medium for culturing the transformant obtained using a microbe, such as Escherichia coli or yeast, as the host, any natural or synthetic medium can be used provided that it contains a carbon source, a nitrogen source, and inorganic salts, etc. that the microbe can utilize, and that it can efficiently culture the transformant. For the carbon source, carbohydrates such as glucose, fructose, sucrose, starch, or cellulose; organic acids such as acetic acid or propionic acid; or alcohols such as ethanol or pronpanol can be used. For the nitrogen source, ammonium salts of inorganic or organic acids, such as ammonium chloride, ammonium sulfide, ammonium acetate, or ammonium phosphate; other nitrogen-containing compounds; peptone; meat extract; or corn steep liquor can be used. For the inorganics, potassium phosphate, magnesium phosphate, magnesium sulfate, sodium chloride, ferrous sulfate, manganese sulfate, copper sulfate, or calcium carbonate, etc. can be used.

Culturing is usually performed under an aerated condition, such as shake culture or aerobic agitation culture, at 30° C. for 6 to 24 hours. During culturing, the pH level should preferably be maintained between 2.0 and 6.0. The pH level can be adjusted using an inorganic or organic salt, an alkaline solution, or the like. During culturing, an antibiotic, such as ampicilin or tetracycline, may be added to the medium as needed.

For the medium for culturing the transformant obtained using an animal cell as the host, an RPMI1640 medium or a DMEM medium, which are commonly used, or a medium consisting of either of these with bovine fetal serum or the like added to it may be used. Culturing is normally performed under the presence of 5% $CO_2$ at 37° C. for 1 to 30 days. During culturing, an antibiotic such as kanamycin or penicillin may be added to the medium as needed.

Culturing can be performed using a batch method or a continuous method. For the culturing method, a method can be used that obtains lactic acid in the form of a lactate, such as ammonium lactate or calcium lactate, while neutralizing the lactic acid with an alkali such as ammonium or calcium salt. A method that obtains lactic acid as free lactic acid can also be used.

After culturing is finished, various types of ordinary refining methods can be used in combination for separating the lactic acid, which is a gene product, from the cultured product. For example, if lactic acid is produced inside transformed cells, the gene product can be separated from the cells using a regular method, such as ultrasound destruction, grinding, or pressure crushing, to destroy the cells of the bacteria. In this case, protease should be added as needed. If lactic acid is produced in the culture supernatant, solids are removed from this solution through filtering, centrifugal separation, or the like.

For example, after the culturing process is finished, the cultured liquid can be separated into solid and liquid through at least a single solid-liquid separation process, such as belt pressing, centrifugal separation, or filter pressing. It is preferable to apply a refining process to the separated filtrate. In the refining process, electrodialysis, for example, can be used to remove organic acids and sugars other than lactic acid from the filtrate containing lactic acid and to obtain a lactic acid solution or ammonium lactate solution. If an ammonium lactate solution is obtained, ammonium can be decomposed using a bipolar membrane, etc. to produce an aqueous solution of lactic acid and aqueous ammonia. If the amount of organic acids and sugars other than lactic acid in said filtrate is small, it is also possible to skip electrodialysis, concentrate the liquid by evaporating the moisture as needed, and then use a bipolar membrane.

Note that for the cultured liquid and crudely extracted fractions, various refining and separation methods, such as separation and extraction using an organic solvent and distillation, can be used in addition to the aforementioned methods to refine lactic acid or its salt. Furthermore as needed, various types of lactic acid derivatives can be obtained by applying esterization, lactid conversion, olygomerization, or prepolymerization to the cultured liquid, crudely extracted fraction, or its refined product. As needed, lactic acid, its salt, and one or more kinds of lactic acid derivatives can be collected from the lactic acid fermentation liquid.

Embodiments

Although embodiments of the present invention are described below, they are not intended to specifically limit the scope of the present invention.

Embodiment 1

Design of the DNA Sequence of L-lactate Dehydrogenase Gene

In order to efficiently produce L-lactate dehydrogenase, which is derived from bovine, a high eucaryote, in the Saccaromyces cerevisiae family of yeast, we designed a new, non-naturally occurring gene sequence for the DNA that codes the amino acid sequence of the bovine-derived L-lactate dehydrogenase.

1) The codon that is often used in *Saccaromyces cerevisiae* was used.
2) Kozaks sequence (ANNATGG) was added straddling the start codon.
3) Unstable sequences and repeated sequences in mRNA were eliminated as much as possible.
4) The GC content deviation was made uniform over the entire region.
5) Measures were taken to ensure that restriction enzyme sites, not suitable to gene cloning, would not be created inside the designed sequence.
6) Restriction enzyme EcoRI, XhoI, and AflIII sites, which are useful for the two ends to be incorporated into the chromosome incorporation type vector, were added.

For the codon usage frequency in yeast, the *Saccaromyces cerevisiae* codon usage obtained from the codon usage database (http://www.kazusa.or.jp/codon/) is shown in FIG. 2. In this figure, the codons that are used frequently for specific amino acids are identified (the underlined codons).

A new DNA sequence (999 bp) for coding a protein having the LDH activity obtained based on the design guidelines in 2) through 5) above and by applying the frequently used codon in the codon usage shown in FIG. 1 (hereafter referred to as "LDHKCB gene") is shown in SEQ ID NO:3. Additionally, a DNA sequence (1052bp) that includes the DNA sequence shown in SEQ ID NO:3, as well as the upstream side of its start codon and the downstream side of its stop codon (hereafter referred to as "LDHKCB sequence"), is shown in SEQ ID NO:4.

In the DNA sequence shown in SEQ ID NO:3, codons that were different from those used in the original DNA sequence were used in all amino acids except methionine. Note that the newly adopted codons were all frequently used codons from among those shown in FIG. 1. Furthermore, FIG. 2 shows the result of a computer-based homology analysis of the original bovine-derived LDH gene and the LDHKCB gene. As is clear from FIG. 2, it was discovered that a large number of replacements were needed over almost the entire DNA sequence.

Embodiment 2

Complete Synthesis of the LDHKCB Sequence

In this embodiment, the method of Fujimoto et al. was used, which is a known method for synthesizing long-chain DNA (Hideya Fujimoto, Synthetic Gene Creation Method, Plant Cell Engineering Series 7, Plant PCR Experiment Protocol, 1997, Shujunsha Co., Ltd., p95-100). The principle behind this method is as follows: oligonucleotide primers of around 100 mer are created so as to have an overlap of between 10 and 12 mer at the 3' end. Then, the missing area is extended using the overlapped region between the oligonucleotide primers, and is amplified through a PCR using the primers at both ends. This operation is sequentially repeated to synthesize the target long-chain DNA. For the PCR amplifier, Gene Amp PCR system 9700 (P.E. Applied Biosystems Inc.) was used.

Specifically, the two kinds of oligonucleotide primers to be linked were mixed first, and a DNA extension reaction was carried out at 96° C. for 2 minutes, 68° C. for 2 minutes, 54° C. for 2 minutes, and 72° C. for 30 minutes under the presence of KOD-plus-DNA polymerase (Toyobo). Next, using ¹⁄₁₀ of the sample as a mold, a PCR (polymerase chain reaction) was carried out. In this reaction, the sample was first kept at 96° C. for 2 minutes; it was then put through 25 cycles (with each cycle consisting of 96° C. for 30 seconds, 55° C. for 30 seconds, and 72° C. for 90 seconds) under the presence of primers at both ends; and finally was kept at 4° C. For the reaction, the buffer and dNTPmix, etc. that came with the DNA polymerase were used.

A series of overlapping PCRs were carried out according to FIG. 3 to create the gene fragments that were ultimately targeted. The DNA sequences of all 28 primers shown in FIG. 3 (BA, B01, BB, B02, BC, B03, BD, B04, BE, B05, BF, B06, BG, B07, BH, B08, BI, B09, BJ, B10, BK, B11, BL, B12, BM, B13, BN, and B14) are shown in SEQ ID NOS:5 through 32, respectively. After the base sequence of the synthesized LDHKCB gene was verified, a restriction enzyme process using EcoRI was applied. The sequence was then linked to the pCR2.1 TOPO Vector (Invitirogen), to which an enzyme process using EcoRI had been applied in a similar manner, using a normal method. This vector is referred to as the pBTOPO-LDHKCB vector.

Embodiment 3

Construction of a Vector for Yeast Chromosome Incorporation

Figure 4:
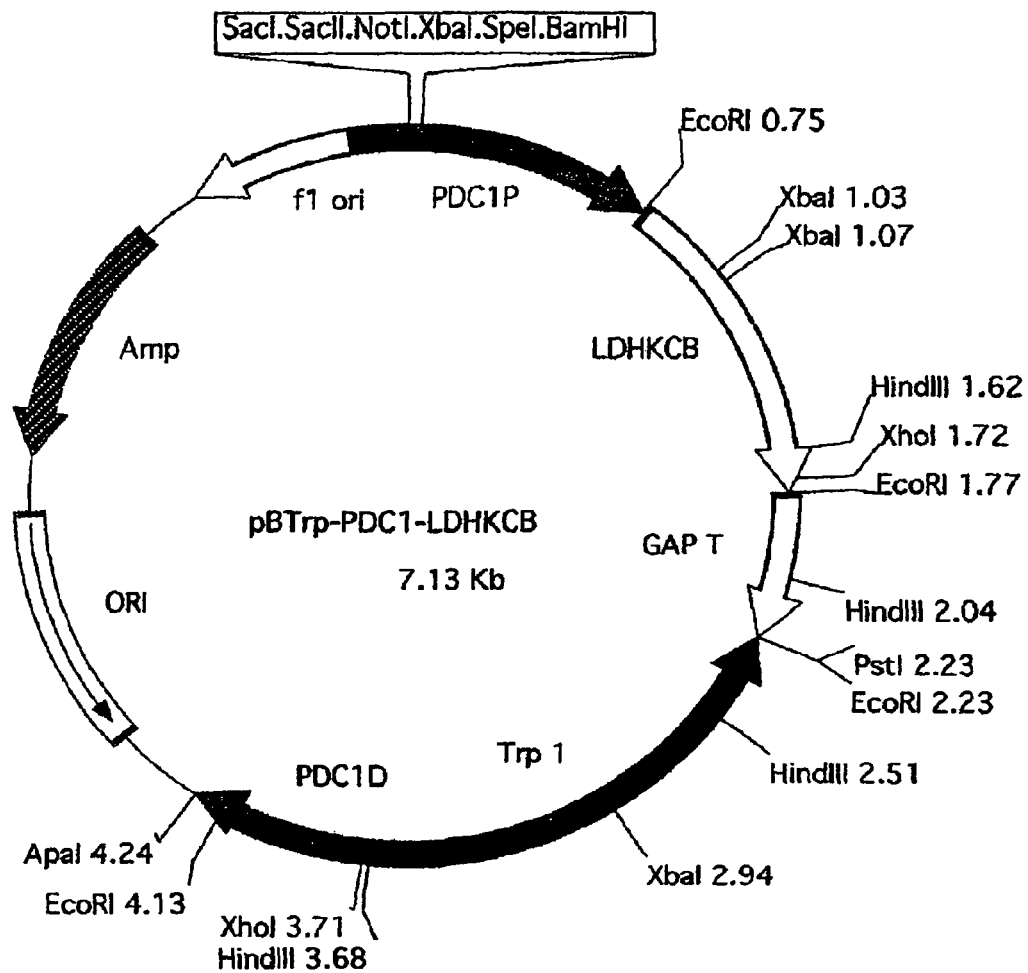
FIG. 4

A yeast chromosome incorporation-type vector was constructed using the LDHKCB sequence completely synthesized in Embodiment 2. This vector is referred to as pBTRP-PDC1-LDHKCB and its plasmid map is shown in FIG. 4.

1. Isolating PDC1P Fragments for Constructing pBTrp-PDC1-LDHKCB

PDC1P fragments were isolated by means of the PCR amplification method that uses the genome DNA of the *Saccaromyces cerevisiae* YPH strain (Stratagene Corp.) as the mold.

The genome DNA of the *Saccaromyces cerevisiae* YPH strain was prepared using the Fast DNA Kit (Bio 101 Inc.), which is a genome preparation kit, and according to the detailed protocol described in the appendix. DNA concentration was measured using the spectrophotometer Ultro spec 3000 (Amersham Pharmacia Biotech Inc.).

For the PCR, Pyrobest DNA Polymerase (Takara Shuzo Co., Ltd.), which is said to produce highly precise amplified fragments, was used as the amplification enzyme. A total of 50 µl of reaction solution, containing a 50 ng/sample of the genome DNA of the *Saccaromyces cerevisiae* YPH strain prepared using the aforementioned method, a 50 pmol/sample of the primer DNA, and a 0.2 units/sample of Pyrobest DNA Polymerase, were prepared. The reaction solution was put through DNA amplification using a PCR amplifier system (Gene Amp PCR system 9700 made by P.E. Applied Biosystems Inc.). The reaction conditions for the PCR amplifier were as follows: the solution was first kept at 96° C. for 2 minutes; it was then put through 25 cycles (with each cycle consisting of 96° C. for 30 seconds, 55° C. for 30 seconds, and 72° C. for 90 seconds); and finally was kept at 4° C. The PCR-amplified fragments were verified to be amplified gene fragments by means of electrophoresis in 1% TBE agarose gel. Note that a synthetic DNA (Sawaday Technology Co.) was used as the primer DNA for the reaction; the DNA sequence of this primer is described below.

A restriction enzyme BamH1 site was added to the PDC1P-LDH-U (31 mer, Tm value of 58.3° C.) end.

```
                                          (SEQ ID NO: 33)
ATA TAT GGA TCC GCG TTT ATT TAC CTA TCT C
```

A restriction enzyme EcoRI site was added to the PDC1P-LDH-D (31 mer, Tm value of 54.4° C.) end.

```
                                          (SEQ ID NO: 34)
ATA TAT GAA TTC TTT GAT TGA TTT GAC TGT G
```

2. Constructing a Recombinant Vector Containing a Promoter and the Target Gene

Under the control of the promoter sequence for pyruvate decarboxylase 1 gene (PDC1) derived from *Saccaromyces cerevisiae*, a bovine-derived L-lactate dehydrogenase gene (LDH gene) was used as the target gene.

The new chromosome incorporation-type vector constructed for constructing the present recombinant vector was named pBTrp-PDC1-LDHKCB. The details of an example of constructing the present vector are described below. An overview of the present embodiment is illustrated in FIGS. 5 through 8. Note that the procedure for constructing the vector is not limited to that described here.

When constructing the vector, the PDC1 gene promoter fragment (PDC1P) 971 bp and the PDC1 gene downstream region fragment (PDC1D) 518 bp were isolated using the PCR amplification method that uses the genome DNA of the *Saccaromyces cerevisiae* YPH strain as the mold, as described above. Although the procedure described above was used for PCR amplification, the following primers were used for amplifying the PDC 1 gene downstream region fragment:

A restriction enzyme XhoI site was added to the PDC1D-LDH-U (34 mer, Tm value of 55.3° C.) end.

```
                                          (SEQ ID NO: 35)
ATA TAT CTC GAG GCC AGC TAA CTT CTT GGT CGA C
```

A restriction enzyme ApaI site was added to the PDC1D-LDH-D (31 mer, Tm value of 54. 4° C.) end.

```
                                          (SEQ ID NO: 36)
ATA TAT GAA TTC TTT GAT TGA TTT GAC TGT G
```

After the PDC1P and PDC1D amplified gene fragments obtained through the aforementioned reactions were each refined through an ethanol precipitation process, the PDC1P amplified fragment and the PDC1D amplified fragment were reacted with restriction enzymes BamHI/EcoRI and XhoI/ApaI, respectively. Note that all of the enzymes used below were made by Takara Shuzo Co., Ltd. Additionally, the series of detailed operations in the ethanol precipitation process and the restriction enzyme processes were based on "Molecular Cloning—A Laboratory Manual, Second Edition" (Maniatis et al., Cold Spring Harbor Laboratory Press, 1989).

Figure 5:
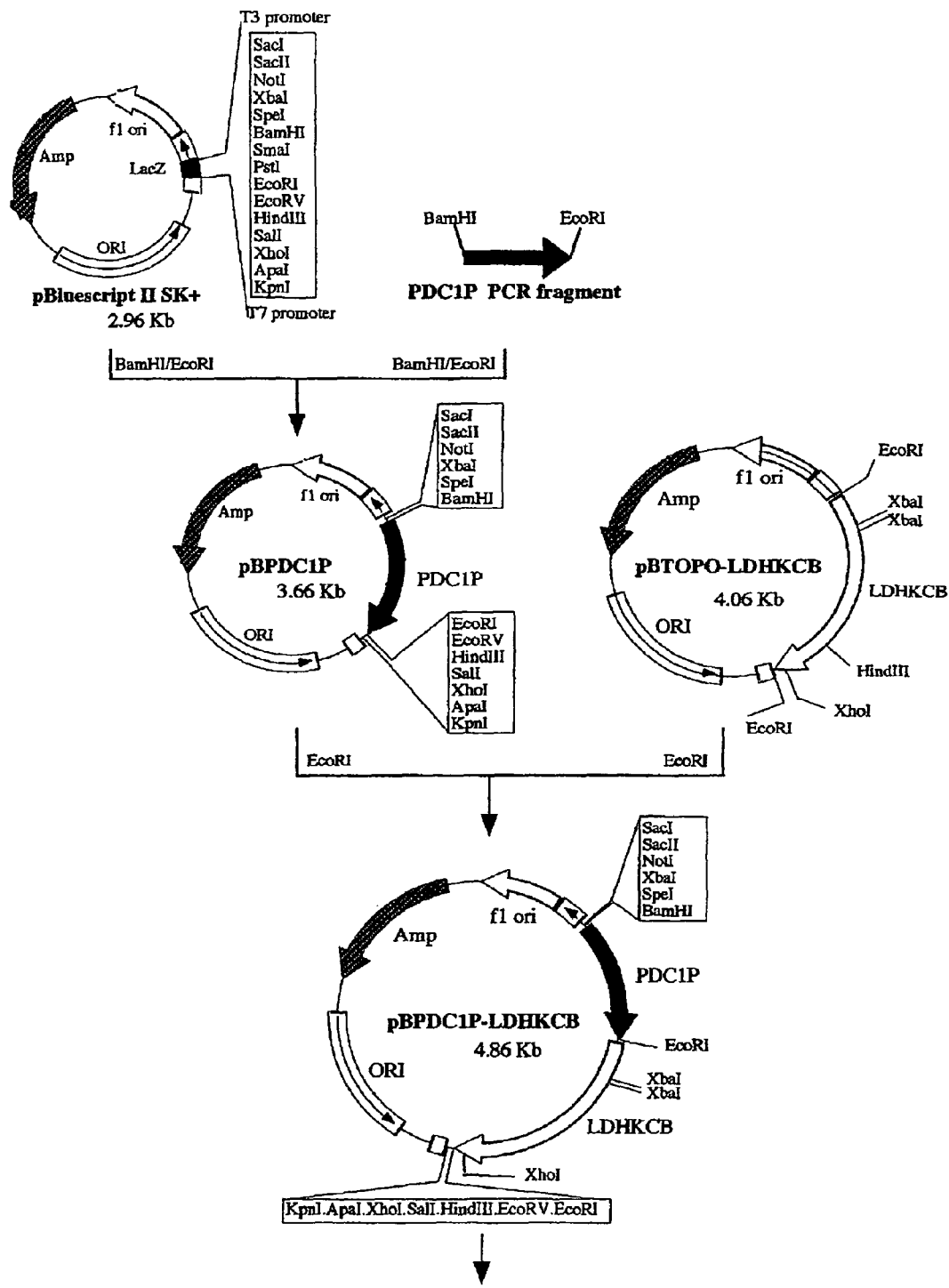
FIG. 5

The series of reaction operations for constructing the vector were carried out according to a generally known DNA subcloning method. That is, the PDC1P fragment, which had been amplified by the aforementioned PCR method and to which a restriction enzyme process had been applied, was linked through a T4 DNA Ligase reaction to the pBluescriptII SK+vector (Toyobo), to which the restriction enzyme BamHI/EcoRI (Takara Shuzo) and the dephosphorylase Alkaline Phosphotase (BAP, Takara Shuzo) had been applied (FIG. 5 top row). For the T4 DNA Ligase reaction, the LigaFast Rapid DNA Ligation System (Promega Corporation) was used, following the included detailed protocols.

Next, transformation to competent cells was carried out using the solution in which the ligation reaction had taken place. For the competent cells, *Escherichia coli* JM109 strain (Toyobo) was used, following the included detailed protocols. The obtained cultured solution was sprayed onto an LB plate containing the antibiotic ampicilin at the rate of 100 μg/ml, and incubated overnight. The colony that grew was verified with the colony PCR method using the primer DNA of the insert fragment, and with a restriction enzyme process for a plasmid DNA solution prepared through miniprep. The target vector (pBPDC1P vector) was then isolated (FIG. 5 middle row).

Next, as shown in the middle row in FIG. 5, the LDHKCB gene fragment, obtained by processing the pBTOPO-LDH-KCB vector constructed by Kabushiki Kaisha Toyota Chuo Kenkyusho with the restriction enzyme EcoRI and the end-modification enzyme T4 DNA polymerase, was subcloned, using the same operation as described above, into the pPDC1P vector likewise processed with the restriction enzyme EcoRI and the terminal modification enzyme T4 DNA polymerase, to create the pBPDC1P-LDHKCB vector (FIG. 5 bottom row).

Figure 6:
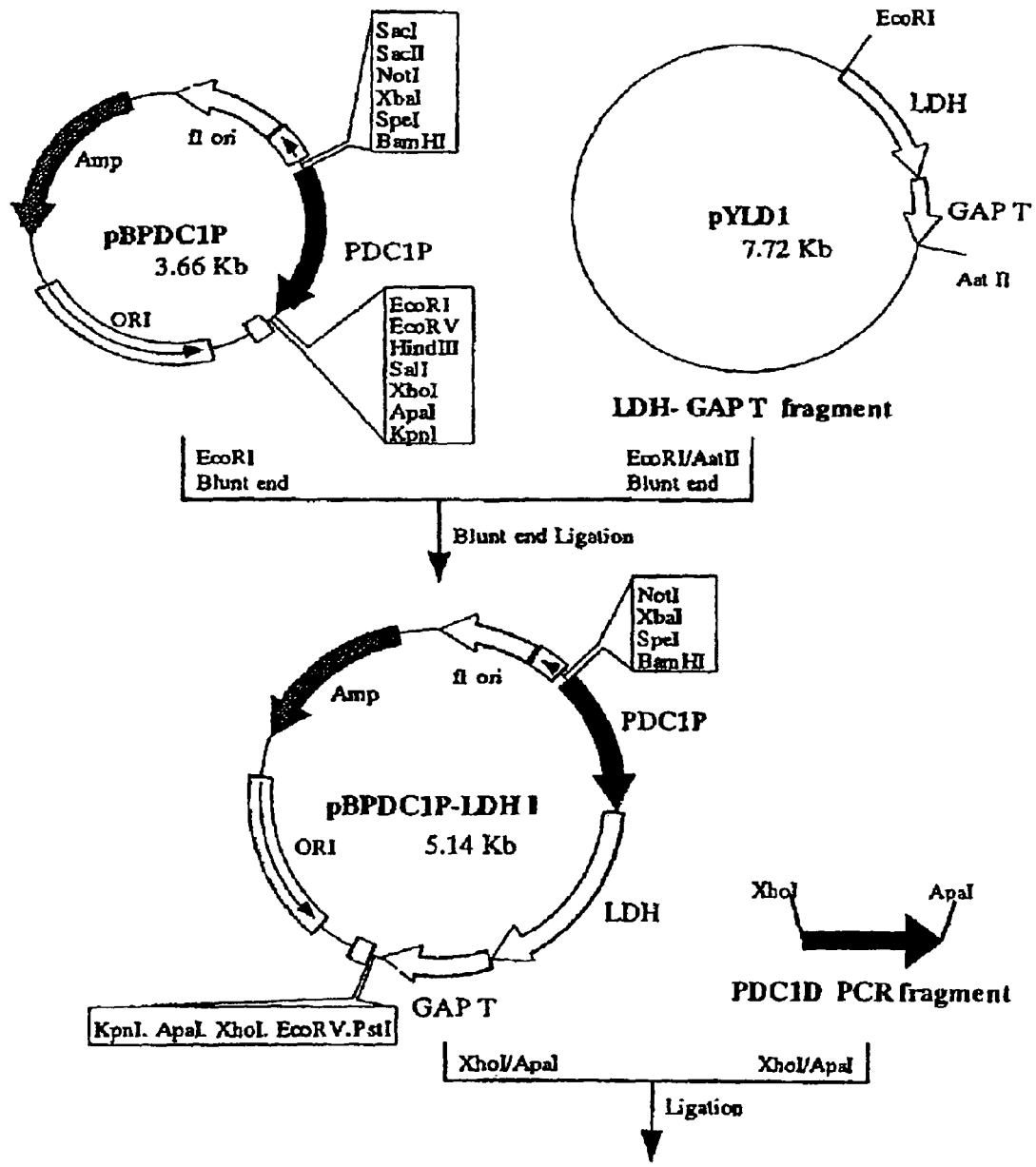
FIG. 6

On the other hand, as shown in FIG. 6, the LDH gene (derived from Bifidobacterium longum) fragment obtained by processing the pYLD1 vector, constructed by Toyota Jidosha Kabushiki Kaisha, with the restriction enzyme EcoRI/AatII and the end-modification enzyme T4 DNA polymerase, was subcloned, using the same operation as described above, into the pBPDC1P vector likewise processed with the restriction enzyme EcoRI and the terminal modification enzyme T4 DNA polymerase, to create the pBPDC1P-LDH1 vector (FIG. 6). Note that the aforementioned pYLD1 vector has been incorporated into *Escherichia coli* (name: *E. coli* pYLD1) and has been internationally deposited with the International Patent Organism Depositary of the National Institute of Advanced Industrial Science and Technology (Chuo No. 6, 1-1-1 Higashi, Tsukuba-shi, Ibaraki-ken, 305-8566 Japan) under deposit No. FERM BP-7423 in accordance with the Budapest Convention (the original deposit date: Oct. 26, 1999).

Figure 7:
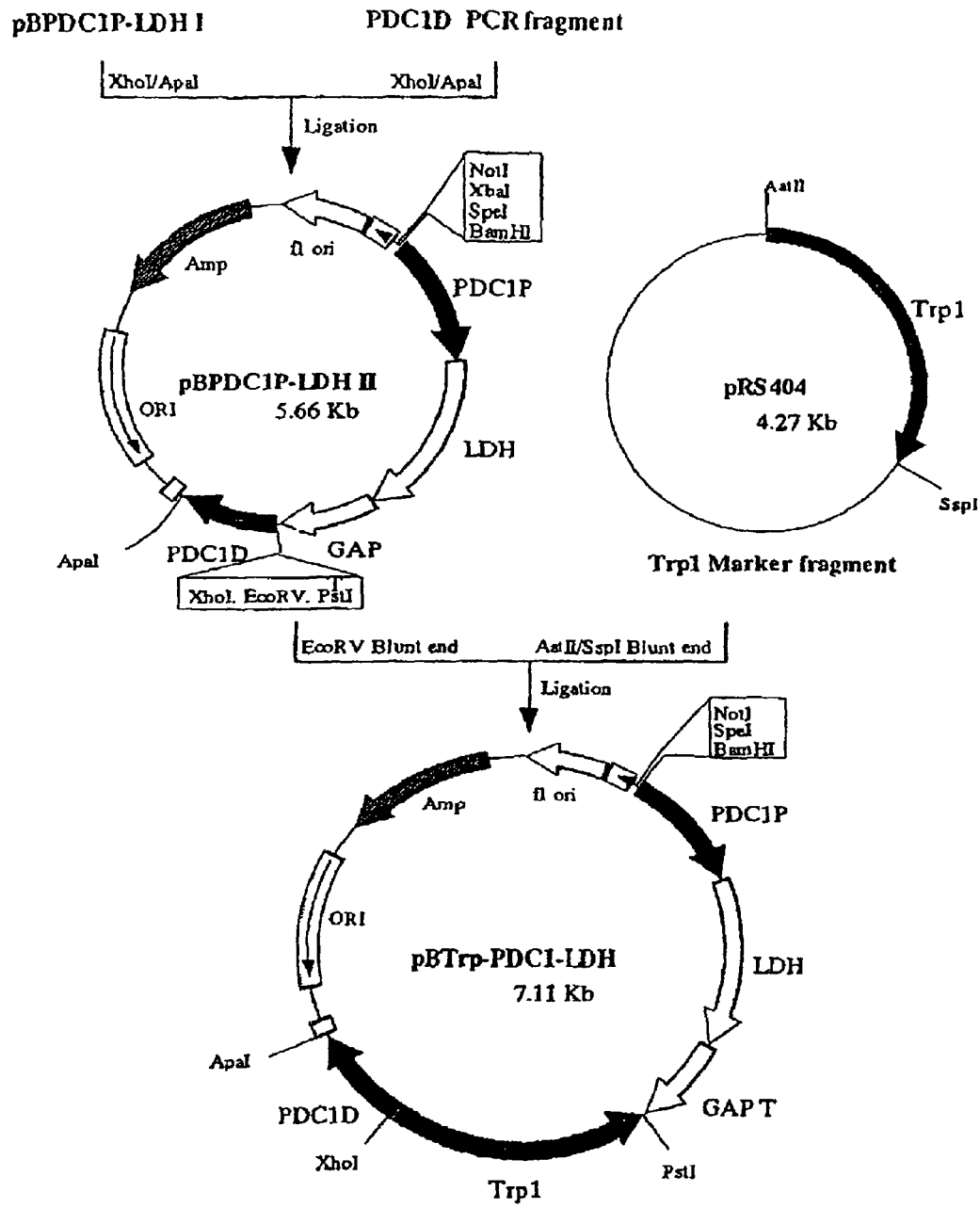
FIG. 7

Next, as shown in FIG. 7, this vector was processed with XhoI/ApaI and was linked to the amplified PDC1D fragment, to which a restriction enzyme had been applied in the same manner, to create the pBPDC1P-LDH vector (FIG. 7 top row). Lastly, the pBPDC1P-LDHII vector, to which a EcoRV process had been applied, was linked to a Trp maker fragment obtained by applying the AatII/SspI process and the T4 DNA polymerase process to the pRS404 vector (Stratagene Inc.), to construct the pBTrp-PDC1-LDH vector.

Figure 8:
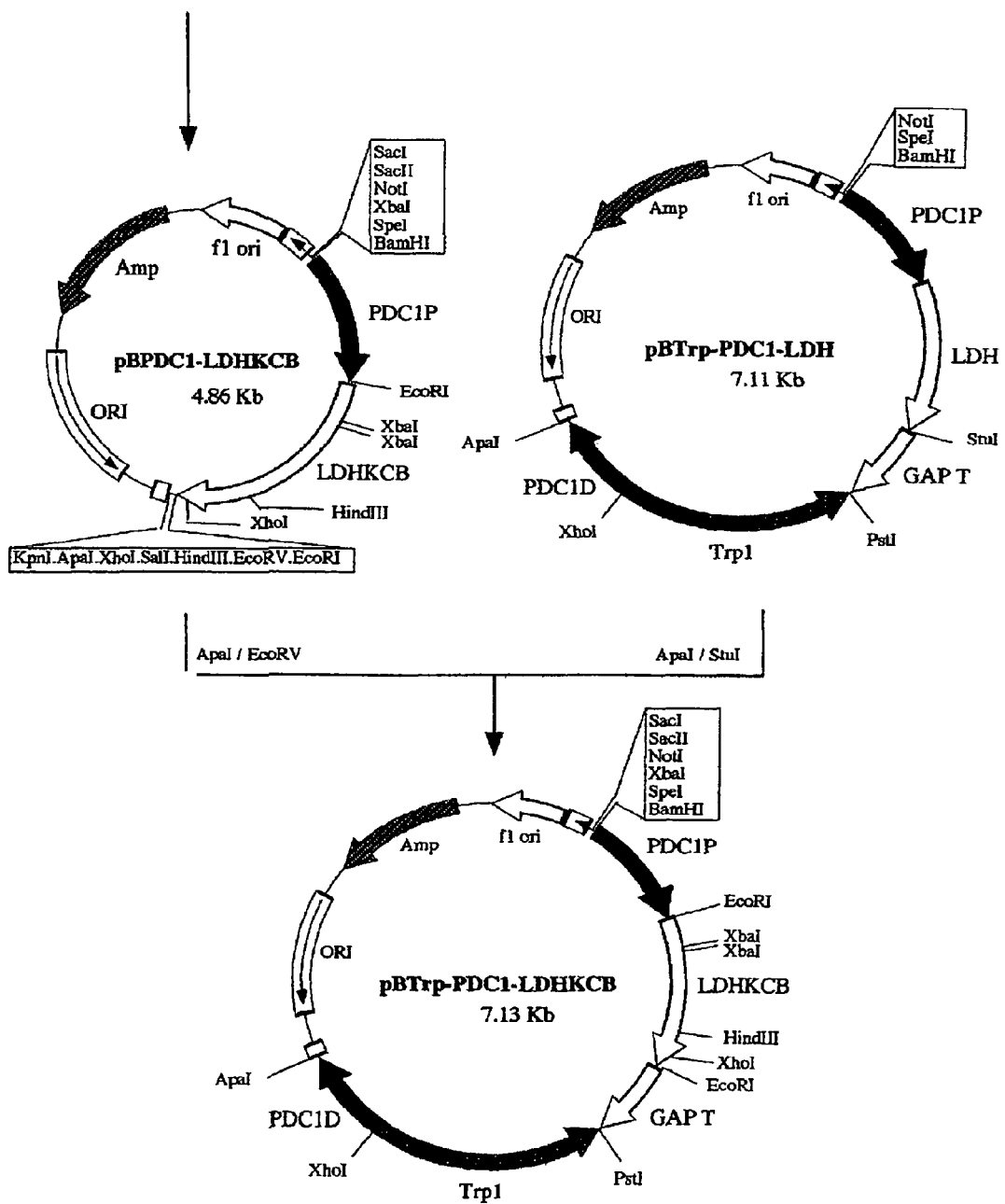
FIG. 8

Next, as shown in FIG. 8, the pBPDC1P-LDHKCB vector was processed with restriction enzymes ApaI/EcoRI; separately, the pBTrp-PDC1-LDH vector was processed into fragments containing the Trp marker processes with restriction enzymes ApaI and StuI. The amplified fragments were linked to construct the chromosome incorporation-type pBTrp-PDC1-LDHKCB vector, which is the final construct.

In order to verify the constructed chromosome incorporation-type pBTrp-PDC1-LDHKCB vector, base sequence determination was performed. An ABI PRISM 310 Genetic Analyzer (P.E. Applied Biosystems Inc.) was used for analyzing the base sequence, and details such as the method of preparing samples and using the instrument were based on the manual provided with the analyzer. The vector DNA to be used as the sample was prepared with an alkali extraction method. Before using this sample, it was first column-refined using the GFX DNA Purification kit (Amersham Pharmacia Biotech Inc.), and then its DNA concentration was measured with the Ultro spec 3000 spectrophotometer (Amersham Pharmacia Biotech Inc.).

Embodiment 4

Transformation of Yeast

The gene incorporates into yeast according to the method developed by Ito et al. (Ito, H., Y. Fukuda, K. Murata and A. Kimura, Transformation of intact yeast cells treated with alkalications, J. Bacteriol. Vol. 153, p 163-168). That is, the yeast IF02260 strain (a strain registered with the Institute of Fermentation, Osaka), from which the tryptophan-synthesizing function had been removed, was cultured in 10 ml YPD medium at 30° C. until it reached the logarithmic growth phase. It was then collected and rinsed with TE buffer. Next, 0.5 ml of TE buffer and 0.5 ml of 0.2M lithium acetate were added, and the mixture was shake-cultured at 30° C. for 1 hour. Then, the chromosome incorporation-type pBTrp-PDC1-LDHKCB vector constructed using the method in Embodiment 3 was processed with restriction enzymes ApaI and SacI (both made by Takara Shuzo), and was added to the culture.

After the present yeast suspension was shake-cultured at 30° C. for 30 minutes, 150 μl of 70% polyethylene glycol 4000 (Wako Pure Chemical Industries) was added and the mixture was agitated well. Then, after the mixture was shake-cultured at 30° C. for 1 additional hour, a heat shock was applied at 42° C. for 5 minutes. The yeast was then rinsed and suspended in 200 μl of water, and this solution was applied to a tryptophan selective culture medium.

The obtained colony was applied to a new tryptophan streak culture medium, and selected strains that had demonstrated stability were checked for gene incorporation using PCR analysis. The genome DNA of the yeast to be used for PCR was prepared by shake-culturing a single colony in 2 ml of YPHD media overnight, collecting the yeast, adding 50 mM Tris-HCL 500 μl and glass beads (425-600 μm, acid washed, SIGMA), and putting the mixture through a vortex at 4° C. for 15 minutes. The supernatant of this solution was put through ethanol precipitation and was dissolved in 50 μl of sterilized water. Using 5 μl of the prepared genome DNA as the mold, PCR was performed in 50 μl of reaction solution. EX Taq DNA Polymerase (Takara Shuzo) was used for the DNA amplification enzyme, and the PCR amplifier Gene Amp PCR system 9700 (P.E. Applied Biosystems Inc.) was used. The reaction condition for the PCR amplifier was as follows: the solution was first kept at 96° C. for 2 minutes; it was then put through 30 cycles (with each cycle consisting of 96° C. for 30 seconds, 55° C. for 30 seconds, and 72° C. for 90 seconds); and finally was kept at 4° C. The sequences of the primers used were as follows:

```
                                    (Sequence number 37)
LDH-KCB-U : TGG TTG ATG TTA TGG AAG AT (20 mer)

(Sequence number 38)
LDH-KCB-D : GAC AAG GTA CAT AAA ACC CAG (21 mer)

(Sequence number 39)
PDC1P-U3  : GTA ATA AAC ACA CCC CGC G (19 mer)
```

Figure 9:
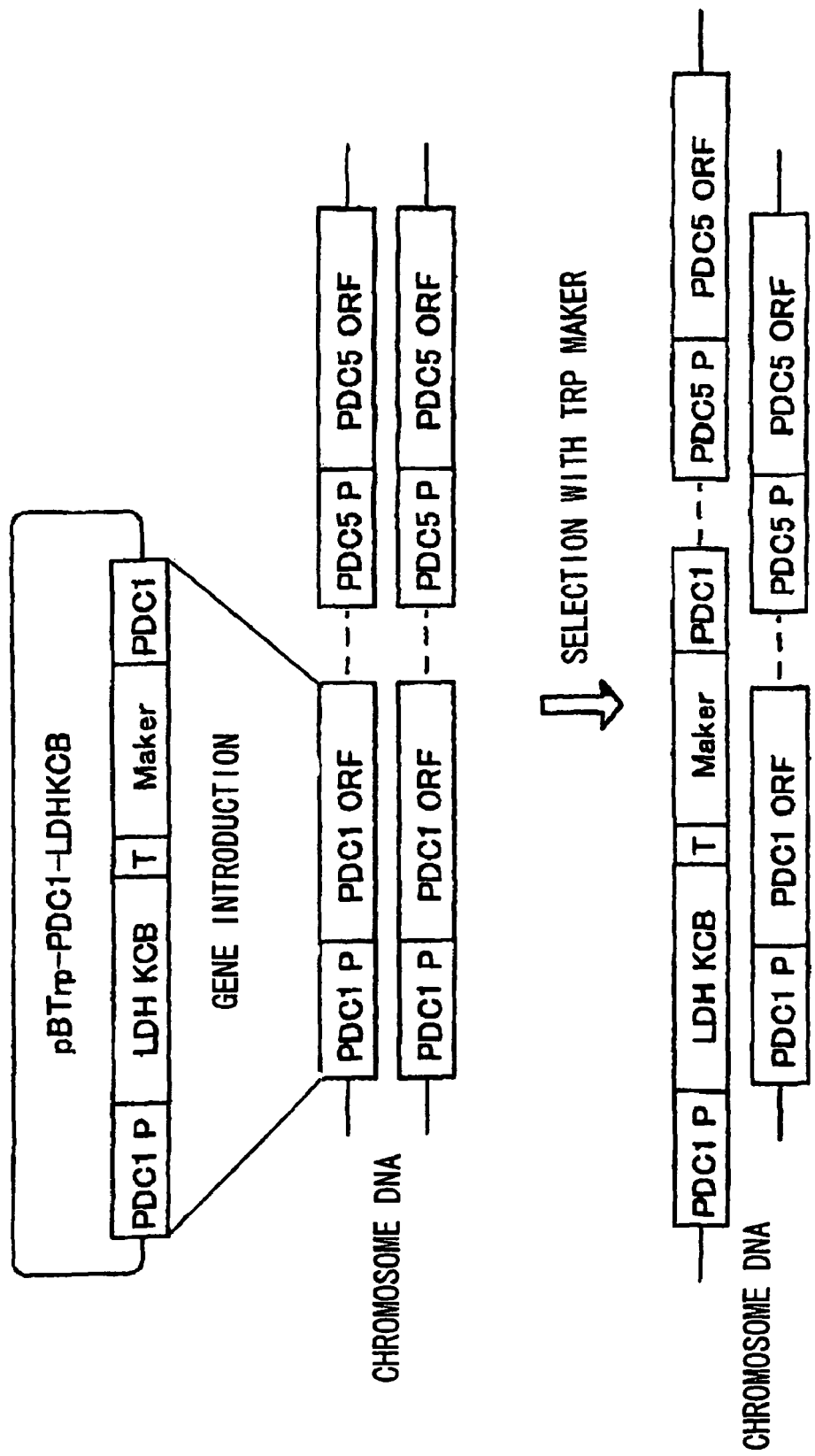
FIG. 9

Those strains that possess a stable tryptophan-synthesizing function and for which PCR was verified under these primers were judged to be transformants into which the LDHKCB gene had been appropriately incorporated. In the present embodiment, three kinds of yeast strains, namely KCB-27, KCB-210, and KCB-211, were obtained as such transformants. FIG. 9 shows the genome chromosome structures of these yeast *Saccaromyces cerevisiae* transformants.

Embodiment 5

Measurement of L-lactic Acid Production Volume in the Transformants

Fermentation experiments were conducted on the three kinds of transformants created. As pre-culturing, the transformants were cultured overnight in a YPD solution medium with 2% glucose concentration. After the yeast were collected and rinsed, they were planted in a YPD solution medium with 15% glucose concentration such that the yeast concentration was 1% (0.5 g/50 ml), and were left to ferment at 30° C. for several days. This fermented solution was sampled every 24 hours and the volume of L-lactic acid contained was estimated[sic]. For measuring the volume produced, Biosensor BF-4 (Oji Scientific Instruments) was used following the detailed measurement methods described in the user's manual for the instrument.

Figure 10:
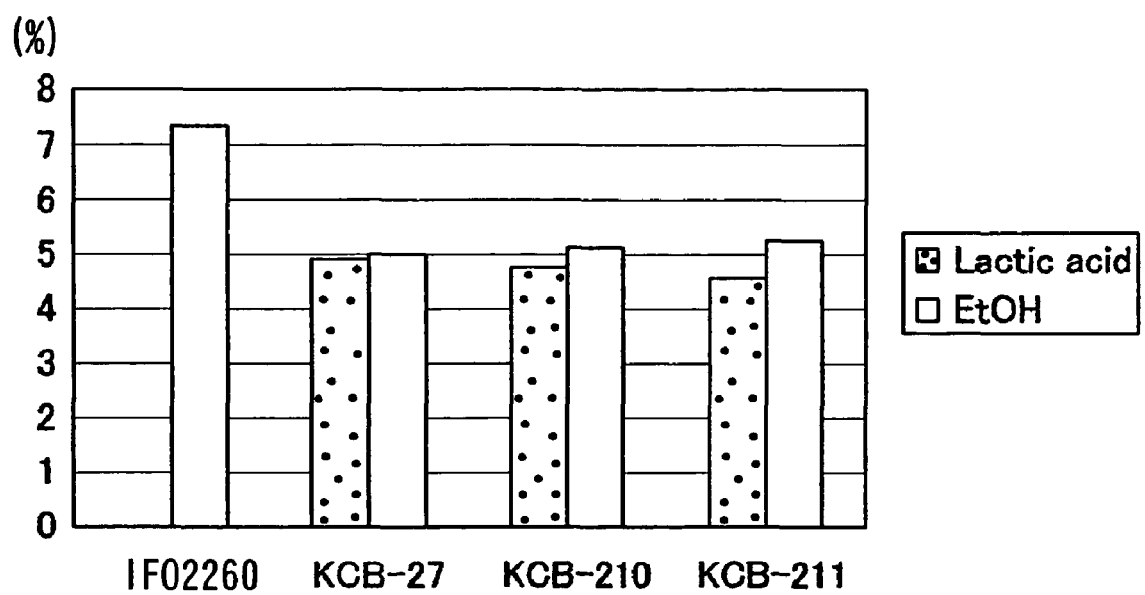
FIG. 10
Figure 11:
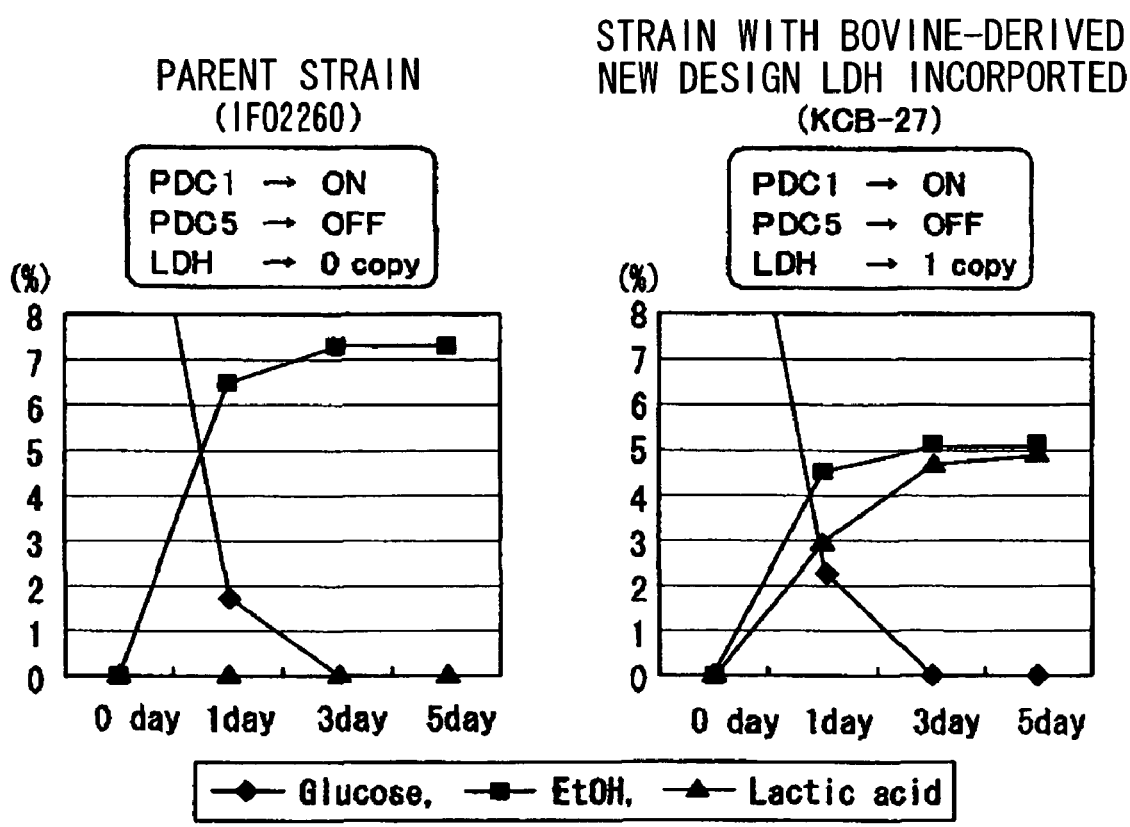
FIG. 11

FIG. 10 and Table 1 show the measurement results of the L-lactic acid volume and the ethanol volume in the cultured solution on the third day of fermentation with a glucose concentration of 15%. As for the KCB-27 strain, FIG. 11 and Table 2 show the trends in L-lactic acid volume and ethanol volume between the $0^{th}$ and $5^{th}$ days.

TABLE 1

| | Production volume (%) | |
| Strain | Lactic acid | Ethanol |
| --- | --- | --- |
| IF02260 | 0 | 7.34 |
| KCB-27 | 4.92 | 5.01 |
| KCB-210 | 4.78 | 5.14 |
| KCB-211 | 4.57 | 5.26 |

TABLE 2

| Strain | Production volume (%) | Number of days passed | | | |
| | | 0 | 1 | 3 | 5 |
| --- | --- | --- | --- | --- | --- |
| IF02260 | Glucose | 15 | 1.84 | 0 | 0 |
| | Lactic acid | 0 | 0 | 0 | 0 |
| | Ethanol | 0 | 6.69 | 7.21 | 7.38 |
| KCB-27 | Glucose | 15 | 2.2 | 0 | 0 |
| | Lactic acid | 0 | 3.01 | 4.73 | 4.92 |
| | Ethanol | 0 | 4.69 | 5.11 | 5.06 |

Even though only a single copy of the LDHKCB gene had been incorporated into each of the transformants into which the LDHKCB gene was incorporated (KCB-27, KCB-210, and KCB-211 strains), production of between 4.5 and 5.0% (45.0 to 50.0 g) of L-lactic acid was confirmed in each 1 L of the culture solution. Meanwhile, ethanol production was 5%, which was approximately 2.5% less than would be expected with the parent strain.

This result clearly indicates an extremely significant increase in the production of L-lactic acid in *Saccaromyces cerevisiae* as compared to the cases reported in the past. Furthermore, this increase in production volume is presumed to be due to the introduction of LDH with substrate affinity equal to or higher than the pyruvic acid substrate affinity of the pyruvate decarboxylase derived from yeast. It is also presumed that introducing LDH under the control of the Pyruvate decarboxylase 1 gene promoter on the chromosome contributed as well.

The above result shows that even a single copy can produce a significant increase in the production volume. Therefore, it can be presumed that the introduction of two or more copies would increase the production volume even further.

Embodiment 6

Measurement of the Pyruvic Acid Substrate Affinity (Michaelis Constant and Km Value) of the L-lactate Dehydrogenase Derived from Various Eucaryotes The pyruvic acid substrate affinity (Michaelis constant and Km value) of the L-lactate dehydrogenase derived from bovine was measured using the method described below. The result was compared to the pyruvic acid substrate affinity of the L-lactate dehydrogenase derived from *Lactobacillus*.

To measure the pyruvic acid substrate affinity (Km value), pyruvic acid, NADH, and FBP were first added to refined L-lactate dehydrogenase to cause a fermentation reaction. Then, the reduction rate of NADH was determined with a spectrophotometer (Ubest-55 made by JASCO) at ABS: 340 nm, and the activity of each L-lactate dehydrogenase was determined.

Next, based on the value of the L-lactate dehydrogenase activity at various pyruvic acid concentration levels, a Lineweaver-Burk plot was created computed from the pyruvic acid saturation curve and the individual inverse numbers. The pyruvic acid substrate affinity (Michaelis constant and Km value) of the L-lactate dehydrogenase was then determined.

A solution prepared by adding 50 mM MOPS buffering solution (made by Narakai) with its pH adjusted to 7.0, 0.15 mM NADH (made by SIGMA), and 1 mM FBP (SIGMA) to 0.05 μg of refined bovine muscle-derived L-lactate dehydrogenase (SIGMA) was kept at 37° C. for 2 to 3 minutes.

Next, pyruvic acid (Wako Pure Chemical Industries) at various concentration levels (0.01 to 100 mM) was added. After quick mixing, the solution was set in a spectrophotometer (Ubest-55 made by JASCO) and the change in absorbance over 1 minute was determined at ABS: 340 nm.

Note that the LDH activity was determined using the following formula (Mathematical expression 5):
[Mathematical Expression 5]

$$LDH \text{ activity value (U/mg protein)} = \frac{\text{Absorbance change over 1 minute}}{0.0063} \times \frac{1000 \mu g}{0.05 \mu g} \times \frac{200 \mu l}{1000 \mu l} \times \frac{1}{1000}$$ [Mathematical expression 5]

Note that the operation was carried out in accordance with 1) Minowa T., Iwata S., Sakai H., and Ohta T., Sequence and characteristics of the *Bifidobacterium longum* gene encoding L-lactate dehydrogenase and primary structure of the enzyme; a new feature of the allosteric site., Gene, 1989, Vol. 85, 161-168; and 2) the description in the user's manual included with SIGMA Lactate Dehydrogenase (LDH/LD).

Figure 12:
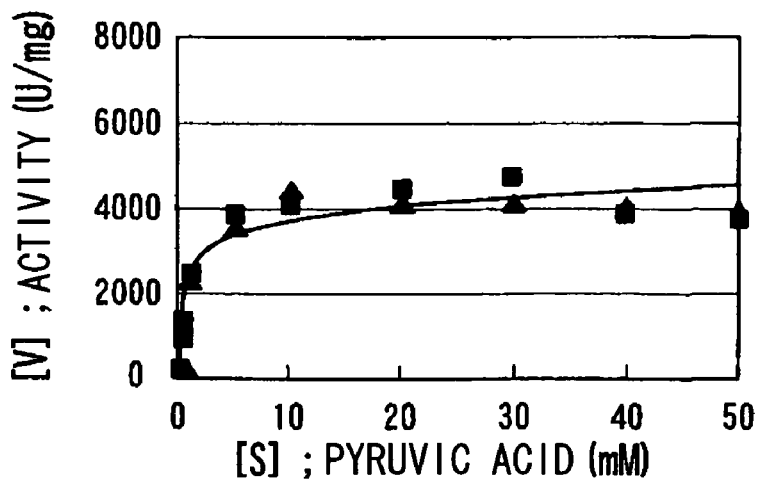
FIG. 12

Based on the LDH activity obtained, a pyruvic acid saturation curve was created with [V]=LDH enzyme accuracy (U/mg) on the vertical axis and [S]=pyruvic acid concentration (mM) on the horizontal axis. This graph is shown in FIG. 12.

Figure 13:
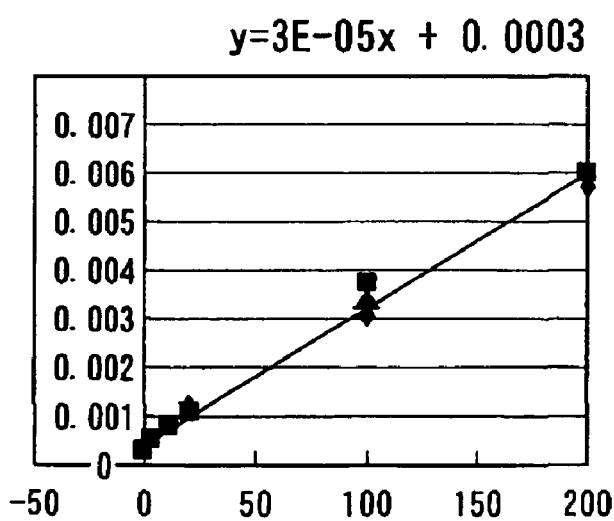
FIG. 13

Furthermore, a Lineweaver-Burk plot computed from individual inverse numbers was respectively created with 1/[V] and 1/[S] on the vertical and horizontal axes. FIG. 13 shows this plot for the present enzyme.

The pyruvic acid concentration substrate affinity (Km value) was computed utilizing the fact that the intersection between the Lineweaver-Burk plot and the 1/[V] axis is 1/Vmax and the intersection between the plot and the 1/[S] axis is −1/Km.

Each Lineweaver-Burk plot showed that the pyruvic acid substrate affinity of the L-lactate dehydrogenase derived from bovine muscle was 0.1 mM. The inventors of the present invention possess the knowledge that the pyruvic acid substrate affinity of the L-lactate dehydrogenase derived from the *Lactobacillus Bifidobacterium longum* is 1.0 mM.

Figure 14:
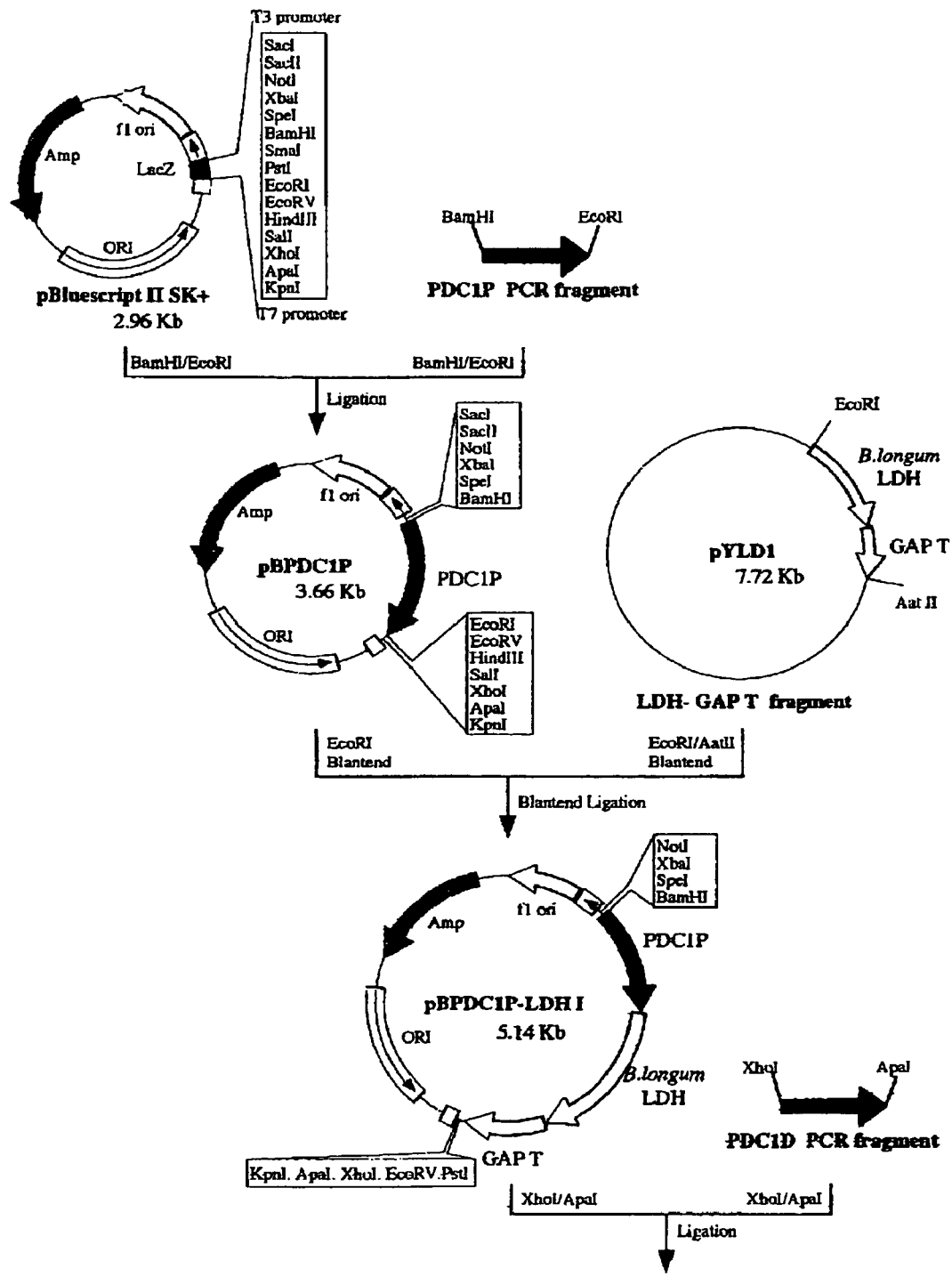
FIG. 14
Figure 15:
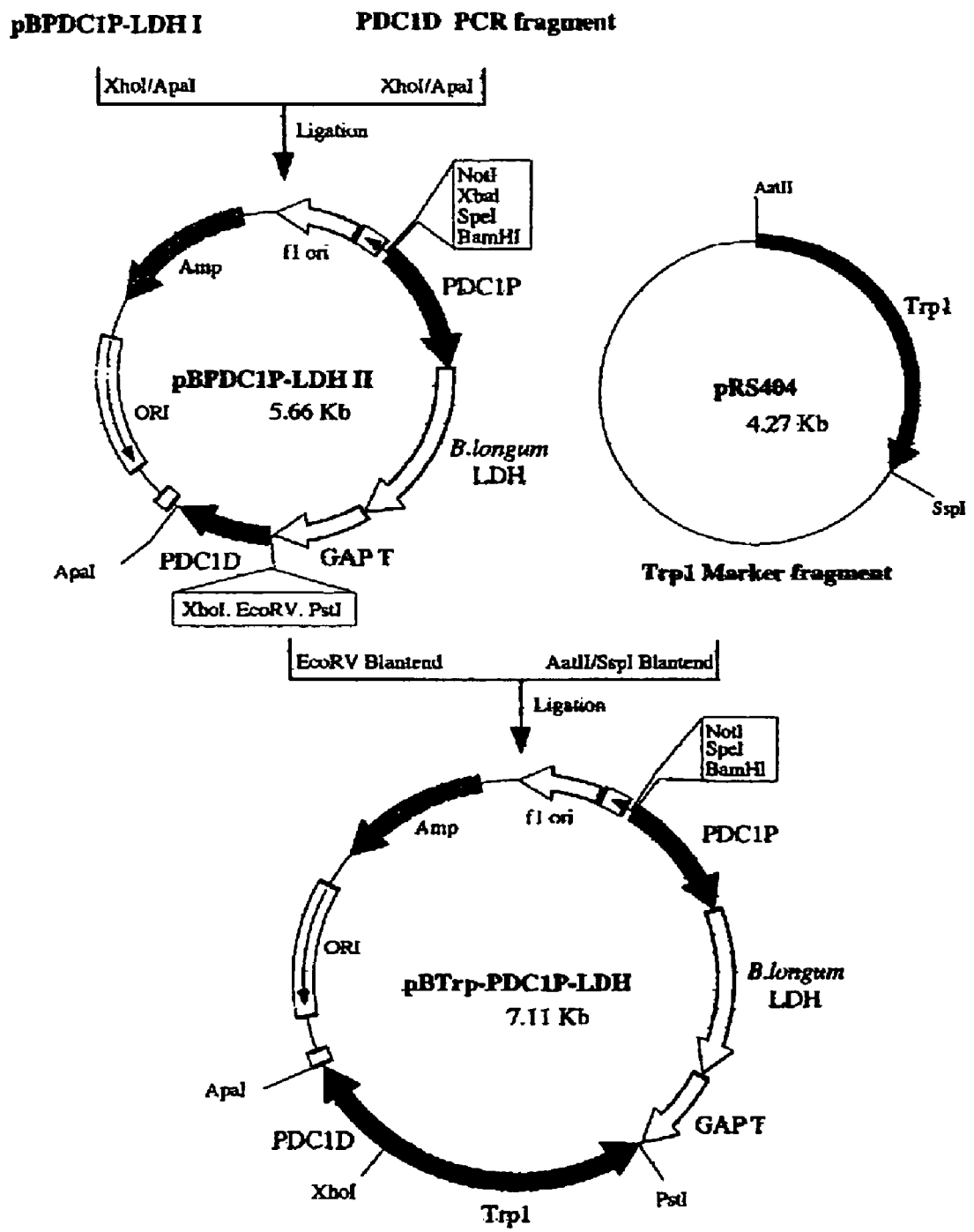
FIG. 15

The volumes of L-lactic acid and alcohol produced by a recombinant yeast obtained by incorporating the DNA for coding the L-lactate dehydrogenase derived from the *Lactobacillus Bifidobacterium longum* into a host and letting it express itself to a high degree are described below. (The fermentation conditions were 30° C. for 3 days in a YPD medium with 15% glucose concentration.) FIGS. 14 and 15 show the vector (pBTrp-PDC1P-LDH; 7.11 kb) for obtaining said *Lactobacillus*-derived recombinant yeast and the process for constructing it. In said transformed yeast, said gene was controllably incorporated by the PDC1 promoter through knock-in into the PDC gene locus on the host chromosome. It has been confirmed that this transformed yeast is a 2-copy body into which said L-lactate dehydrogenase genes have been incorporated into a pair of PDC gene loci on the host chromosome. Note that the operations for constructing said vector and transforming the yeast are the same as those in Embodiments 3 and 4, except for those steps shown in FIGS. 14 and 15.

As shown in Table 3, when this result is compared with the result obtained from the bovine muscle-derived L-lactate dehydrogenase tested in Embodiment 5, the volume of L-lactic acid produced by the yeast with the bovine muscle-derived LDH incorporated is approximately twice that of the yeast with the *Lactobacillus*-derived LDH incorporated.

TABLE 3

| | Production volume (%) | |
|---|---|---|
| | L-lactic acid | Ethanol |
| Yeast with bovine muscle-derived LDH incorporated (pyruvic acid substrate affinity: 0.1 mM) | 4.92% | 5.01% |
| Yeast with *Lactobacillus Bifidobacterium longum*-derived LDH incorporated (pyruvic acid substrate affinity: 1.0 mM) | 2.46% | 6.11% |

Embodiment 7

Measurement of the Pyruvic Acid Substrate Affinity (Michaelis Constant and Km Value) of the Pyruvate Decarboxylase Derived from Yeast To measure the activity of the yeast-derived pyruvate decarboxylase and the pyruvic acid substrate affinity (Km value), pyruvic acid, NADH, and thiamin were first added to refined pyruvate decarboxylase to cause a fermentation reaction. Then, the reduction rate of NADH was determined with a spectrophotometer (Ubest-55 made by JASCO) at ABS: 340 nm, and the activity of the yeast-derived pyruvate decarboxylase was determined.

Next, based on the value of the pyruvate decarboxylase activity at various pyruvic acid concentration levels, a Lineweaver-Burk plot computed from the pyruvic acid saturation curve and the individual inverse numbers was created, and the pyruvic acid substrate affinity (Michaelis constant and Km value) of the pyruvate decarboxylase was determined.

A solution prepared by adding 34 mM Imidasol HCl buffering solution (made by Wako Pure Chemical Industries) with its pH adjusted to 7.0, 0.15 mM NADH (made by SIGMA), and 0.2 mM Tiamine Pyrophospate (SIGMA) to 0.05 μg of refined yeast-derived pyruvate decarboxylase (SIGMA) was kept at 37° C. for 2 to 3 minutes.

Next, pyruvic acid (Wako Pure Chemical Industries) at various concentration levels (0.01 to 100 mM) was added. After quick mixing, the solution was set in a spectrophotometer (Ubest-55 made by JASCO) and the change in absorbance over 1 minute was determined at ABS: 340 nm.

Note that the PDC activity was determined using the following formula (Mathematical expression 6):
[Mathematical Expression 6]

$$PDC \text{ activity value (U/mg protein)} = \frac{\text{Absorbance change over 1 minute}}{0.0063} \times \frac{1000 \mu g}{0.05 \mu g} \times \frac{200 \mu l}{1000 \mu l} \times \frac{1}{1000}$$  [Mathematical expression 6]

Note that the operation was carried out in accordance with the method described in Pronk, J. T, Steensma, H. Y. and Dijken, J. P., Pyruvate, *Metabolism in Saccaromyces cerevisiae*. Yeast, 1996, Vol. 12, 1607-1633.

Figure 16:
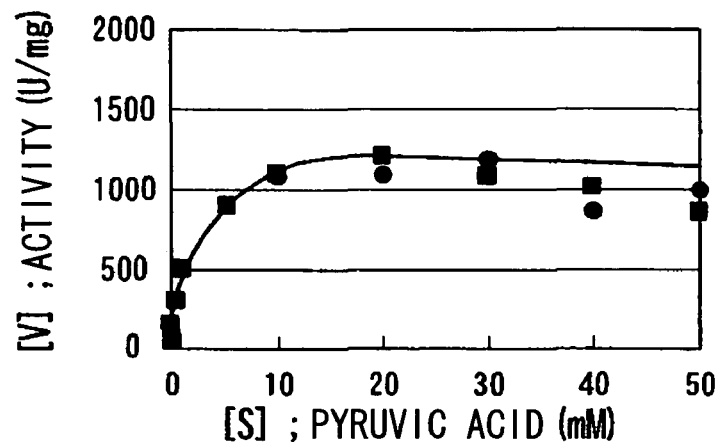
FIG. 16

Based on the PDC activity obtained, a pyruvic acid saturation curve was created with [V]=PDC enzyme accuracy (U/mg) on the vertical axis and [S]=pyruvic acid concentration (mM) on the horizontal axis. This graph is shown in FIG. 16.

Figure 17:
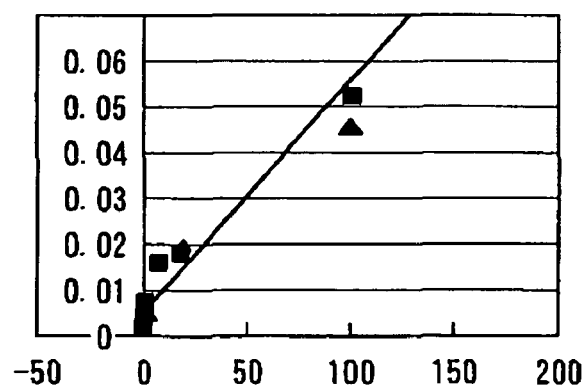
FIG. 17

Furthermore, Lineweaver-Burk plots computed from individual inverse numbers were respectively created with 1/[V] and 1/[S] on the vertical and horizontal axes. These graphs are shown in FIG. 17. The pyruvic acid concentration substrate affinity (Km value) was computed utilizing the fact that the intersection between the Lineweaver-Burk plot and the 1/[V] axis is 1/Vmax and the intersection between the plot and the 1/[S] axis is −1/Km.

The Lineweaver-Burk plot showed that the pyruvic acid Km value of the yeast-derived pyruvate decarboxylase was 0.346 mM.

This value of 0.346 mM is 3.46 times the pyruvic acid Km value of the bovine-derived L-lactate dehydrogenase, which was 0.1 mM in Embodiment 6. In other words, the bovine-derived L-lactate dehydrogenase has 3.46 times the substrate affinity of the yeast-derived pyruvate decarboxylase.

Furthermore, this value of 0.346 mM is 0.346 times the pyruvic acid Km value of the *Bifidobacterium longum*-derived L-lactate dehydrogenase, which was 1.0 mM. In other words, said *Lactobacillus*-derived L-lactate dehydrogenase has only 0.346 times the substrate affinity of the yeast-derived pyruvate decarboxylase.

The publications, including the patents and patent application specifications quoted in this Specification, are made part of this Specification through their quotation in entirety, as though each of these publications were clearly and individually described. Patent application specifications in Japanese patent application numbers 2001-286637, 2002-128323, 2001-287159, 2002-128286, 2002-65880, and 200265879 are also made part of this Specification through their quotation, as though each of these specifications were clearly and individually described.

INDUSTRIAL FIELD OF APPLICATION

The present invention can provide a technology for controlling the production of ethanol and stably mass-producing lactic acid inside a host organism having the pyruvate decarboxylase gene.

[Sequence Table Free Text]

SEQ ID NO:3: Modified DNA for coding Lactate dehydrogenase

SEQ ID NO:4: Modified DNA for coding Lactate dehydrogenase

SEQ ID NOs:5 through 39: Primers

The invention claimed is:

1. A bacterial or yeast transformant into which has been incorporated a lactate dehydrogenase gene coding sequence, wherein the lactate dehydrogenase coding sequence encodes a foreign protein having lactate dehydrogenase activity and pyruvic acid substrate affinity that equals or exceeds the pyruvic acid substrate affinity of the pyruvate decarboxylase inherent in the host organism, wherein a single copy of the lactate dehydrogenase gene coding sequence has been incorporated such that it is under the control of a genomic pyruvate decarboxylase gene promoter on the host chromosome, or such that it is under the control of a structural and functional homologue of the genomic pyruvate decarboxylase gene promoter, which replaces the genomic pyruvate decarboxylase gene promoter on the host chromosome, and wherein the pyruvate decarboxylase gene on the host chromosome is replaced with the single copy of the lactate dehydrogenase gene coding sequence, wherein the foreign protein is coded by the DNA sequence shown in SEQ ID NO:3.

2. The transformant according to claim 1, having the DNA sequence shown in SEQ 1D NO:4 as the DNA sequence for coding the foreign protein.

3. A transformant of the *Saccharomyces* family into which a single copy of a lactate dehydrogenase gene coding sequence has been incorporated, wherein the lactate dehydrogenase gene coding sequence encodes a bovine-derived lactate dehydrogenase or its homologue and has been incorporated such that the single copy of the lactate dehydrogenase gene coding sequence is under the control of a genomic pyruvate decarboxylase 1 gene promoter on the host chromosome of the *Saccharomyces* family, or such that the single copy of the lactate dehydrogenase gene coding sequence is under the control of a structural and functional homologue of the genomic pyruvate decarboxylase 1 gene promoter, which replaces the genomic pyruvate decarboxylase 1 gene promoter on the host chromosome, and wherein the pyruvate decarboxylase 1 gene on the host chromosome has been replaced with the single copy of the lactate dehydrogenase gene coding sequence encoding the bovine-derived lactate dehydrogenase or its homologue, wherein the bovine-derived lactate dehydrogenase or its homologue is encoded by the DNA sequence shown in SEQ ID NO:3.

4. The transformant according to claim 3, having the DNA sequence shown in SEQ ID NO:4 as the DNA sequence for encoding the bovine-derived lactate dehydrogenase or its homologue.

* * * * *